(12) United States Patent
Hungate et al.

(10) Patent No.: US 10,472,670 B2
(45) Date of Patent: Nov. 12, 2019

(54) QUANTITATIVE SUBSTRATE UTILIZATION IN MICROBIAL ECOLOGY USING STABLE ISOTOPE PROBING

(71) Applicant: Arizona Board of Regents on Behalf of Northern Arizona University, Flagstaff, AZ (US)

(72) Inventors: Bruce Hungate, Flagstaff, AZ (US); Egbert Schwartz, Flagstaff, AZ (US); Rebecca Mau, Flagstaff, AZ (US); Jane Marks, Flagstaff, AZ (US)

(73) Assignee: ARIZONA BOARD OF REGENTS ON BEHALF OF NORTHERN ARIZONA UNIVERSITY, Flagstaff, AZ (US)

( * ) Notice: Subject to any disclaimer, the term of this patent is extended or adjusted under 35 U.S.C. 154(b) by 0 days.

(21) Appl. No.: 15/640,028

(22) Filed: Jun. 30, 2017

(65) Prior Publication Data

US 2018/0002745 A1    Jan. 4, 2018

Related U.S. Application Data

(60) Provisional application No. 62/357,266, filed on Jun. 30, 2016.

(51) Int. Cl.
*C12Q 1/6851* (2018.01)
*C12Q 1/6869* (2018.01)
*C12Q 1/6809* (2018.01)
*C12N 15/10* (2006.01)

(52) U.S. Cl.
CPC ....... *C12Q 1/6851* (2013.01); *C12N 15/1003* (2013.01); *C12Q 1/6869* (2013.01)

(58) Field of Classification Search
None
See application file for complete search history.

(56) References Cited

U.S. PATENT DOCUMENTS 7,662,618 B2    2/2010    Halden
8,906,610 B2    12/2014   Brodie et al.

OTHER PUBLICATIONS

Radajewski et al. (2003) Current opinion in Biotechnology vol. 14 :296-302.*
Schwartz (2007) Applied and Environmental Microbiology vol. 73 No. 8 pp. 2541-2546.*
Hayer et al. (2016) Environmental Microbiology Reports doi: 10.1111/1758-2229.12475.*
Dunford et al. (2010) DOI:10.3791/2027; http://www.jove.com/details.php?id=2027.*

(Continued)

*Primary Examiner* — Angela M. Bertagna
(74) *Attorney, Agent, or Firm* — Gavin J. Milczarek-Desai; Quarles & Brady LLP

(57) ABSTRACT

Methods modifying conventional SIP so that isotopic incorporation into the genomes of individual microbial taxa can be quantified are described. Further, methods to quantify the baseline densities of the DNA of individual microbial taxa without exposure to isotope tracers and then to quantify the change in DNA density of each taxon caused by isotope incorporation are described. The distribution of DNA of each taxon along a density gradient reflects the influence of isotope incorporation only, without reflecting the guanine-plus-cytosine content.

10 Claims, 18 Drawing Sheets

Specification includes a Sequence Listing.

(56) References Cited

OTHER PUBLICATIONS

Bell et al. Applied and Environmental Microbiology 2011; 77: 4163-4171 (Year: 2011).*

Stursova et al. FEMS Microbiology Ecology 2012; 80: 735-746 (Year: 2012).*

Miyatake et al. Applied and Environmental Microbiology 2009; 75: 4927-4935 (Year: 2009).*

D. H. Buckley. et al., "Stable Isotope Probing with 15N Achieved by Disentangling the Effects of Genome G+C Content and Isotope Enrichment on DNA Density," Applied and Environmental Microbiology May 2007, pp. 3189-3195.

B. A. Hungate, et al., "Quantitative Microbial Ecology Through Stable Isotope Probing," Applied and Environmental Microbiology, Nov. 2015, vol. 81, pp. 7570-7581.

T. Lueders, et al., "Stable Isotope Probing of rRNA and DNA Reveals a Dynamic Methylotroph Community and Trophic Interactions with Fungi and Protozoa in Oxic Rice Field Soil," Environmental Microbiology, 2004, pp. 60-72.

T. Lueders, et al., "Enhanced Sensitivity of DNA- and rRNA-Based Stable Isotope Probing by Fractionation and Quantitative Analysis of Isopycnic Centrifugation Gradients," Environmental Micrbiology 2004, pp. 71-78.

J. D. Neufeld, et al. "Methodological Considerations for the Use of Stable Isotope Probing in Microbial Ecology," Microbial Ecology, Department of Biological Sciences, University of Warwick, Coventry, UK, Published Oct. 2006, pp. 435-442.

M. Hayer, et al., "Identification of Growing Bacteria During Litter Decomposition in Freshwater Through H218O Quantitative Stable Isotope Probing," Environmental Microbiology Reports, Aug. 1, 2016, 8 pages.

E. Schwartz, et al., "Stable Isotope Probing With 18O-Water to Investigate Microbial Growth and Death in Environmental Samples," Current Opinion in Biothechology, 2016, pp. 14-18.

E. M. Morrisey, et al., "Phylogenetic Organization of Bacterial Activity," The ISME Journal 2016, pp. 1-5.

E. M. Morrisey, et al., "Bacterial Carbon Use Plasticity, Phylogenetic Diversity and the Priming of Soil Organic Matter," The ISME Journal, 2017, pp. 1-10.

* cited by examiner

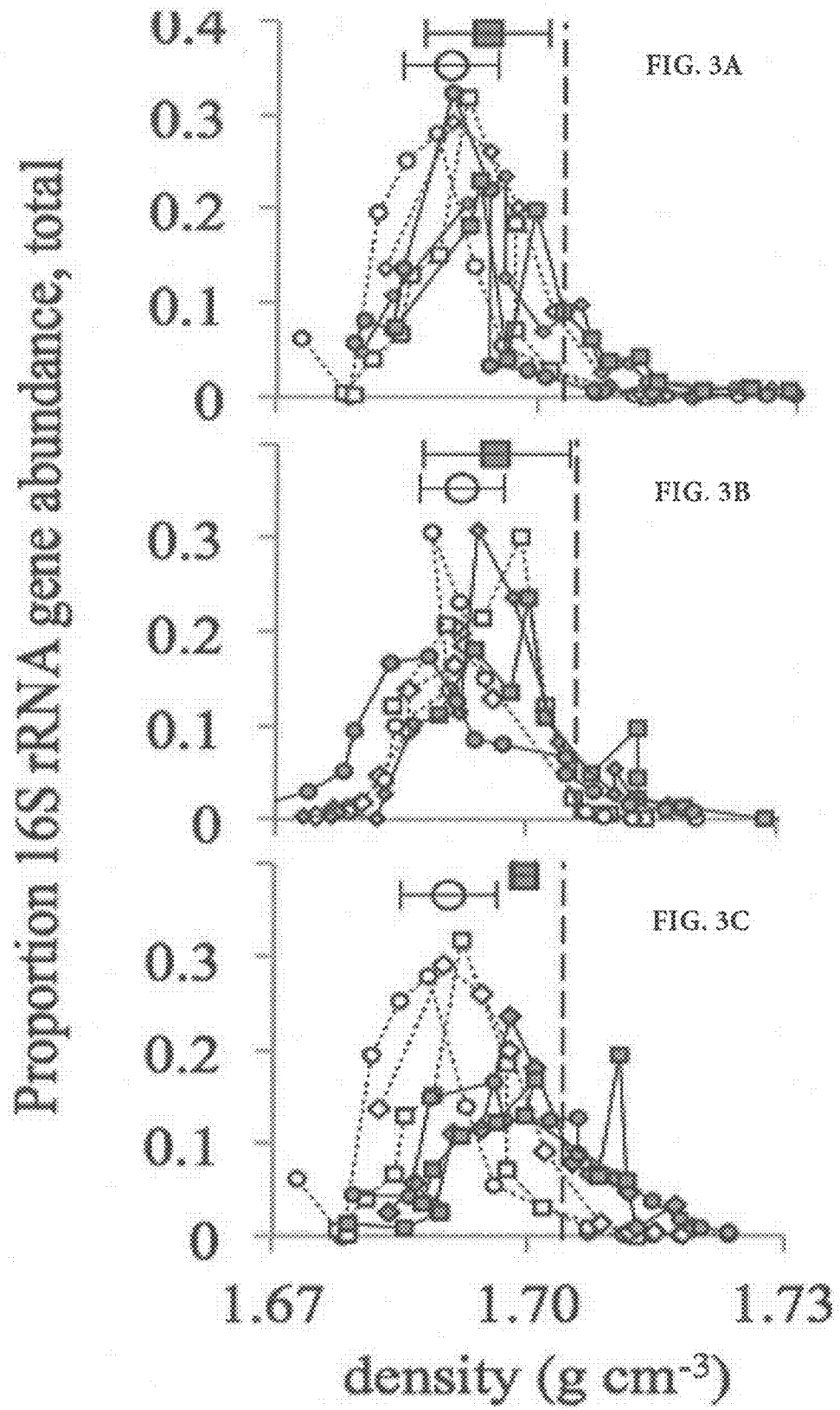

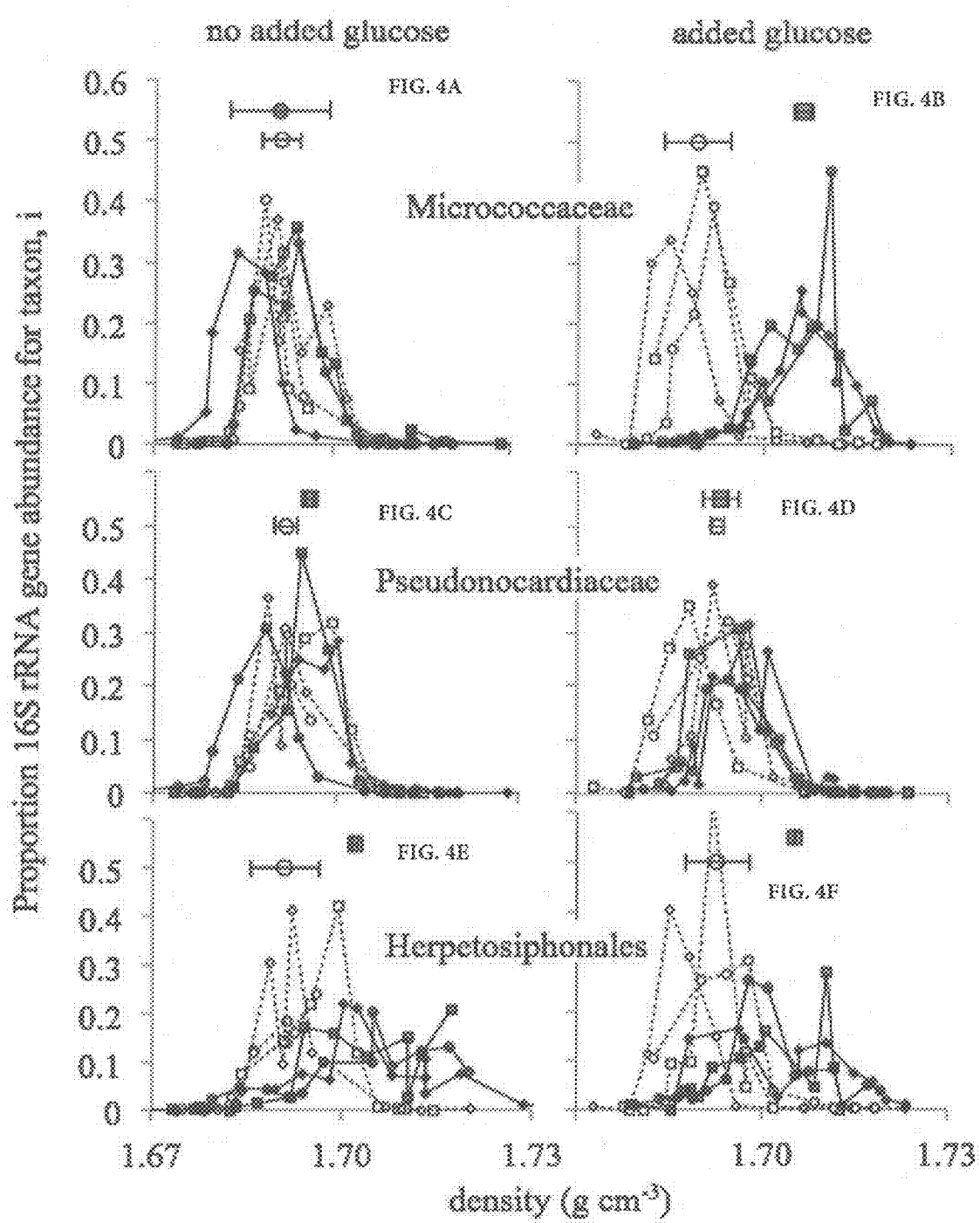

FIG. 8

| Tracer | Mean DNA density (g/cm$^3$) ± SD for taxa that: | |
|---|---|---|
| | Assimilated tracer | Did not assimilate tracer |
| [18O]water | 1.6905 ± 0.0031 | 1.6912 ± 0.0033 |
| [18O]water with glucose | 1.6896 ± 0.0033 | 1.6894 ± 0.0045 |
| [13C]glucose | 1.6890 ± 0.0030 | 1.6900 ± 0.0036 |

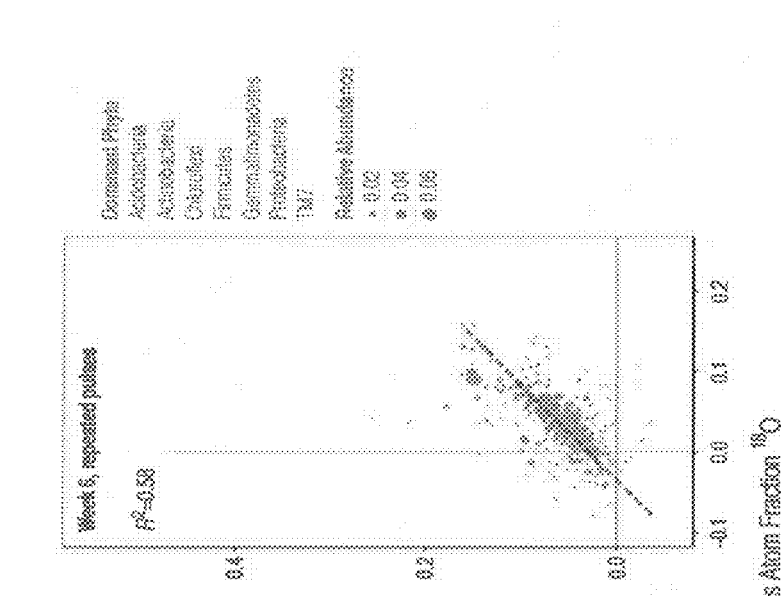
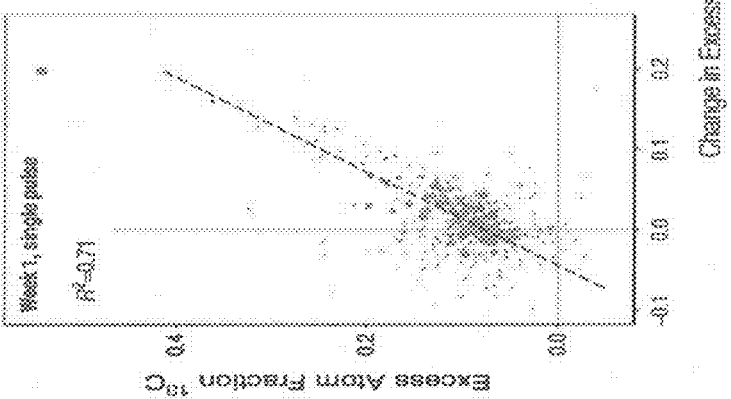
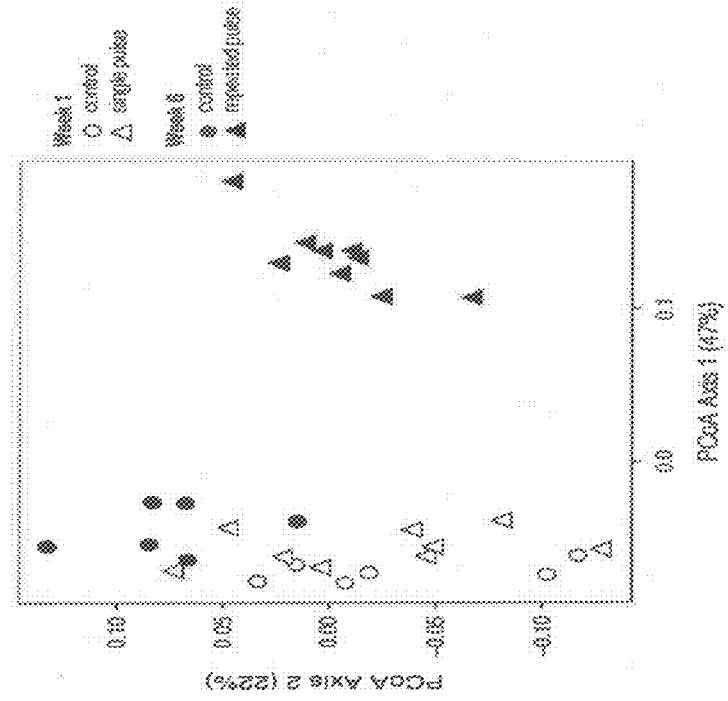
FIG. 10B
FIG. 10A

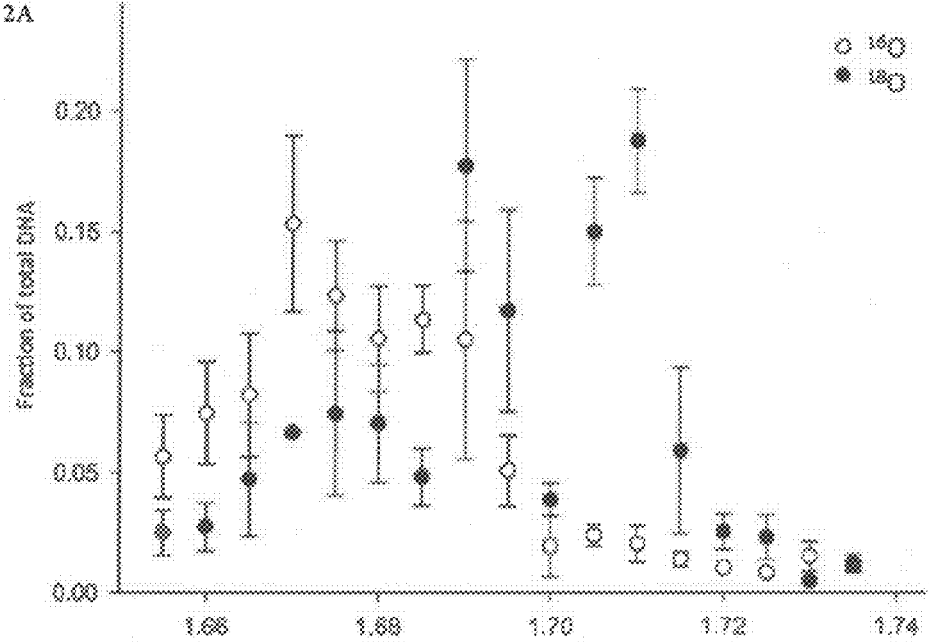
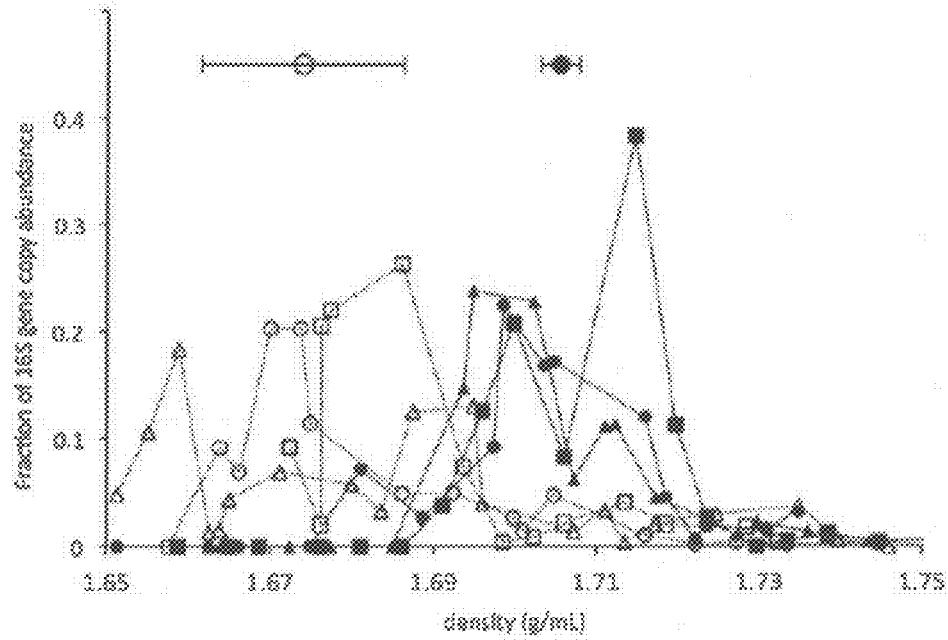

SEQUENCE LISTING

<160> NUMBER OF SEQ ID NOS: 9

<210> SEQ ID NO 1
<211> LENGTH: 16
<212> TYPE: DNA
<213> ORGANISM: Artificial Sequence
<220> FEATURE:
<223> OTHER INFORMATION: Primer

<400> SEQUENCE: 1
cctacgggdg gcwgca                                                      16

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ggactachvg ggtmtctaat c                                                21

<210> SEQ ID NO 3
<211> LENGTH: 14
<212> TYPE: DNA
<213> ORGANISM: Artificial Sequence
<220> FEATURE:
<223> OTHER INFORMATION: Primer

<400> SEQUENCE: 3
cagcagccgc ggta                                                        14

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
actcctacgg gaggcagcag                                                  20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggactachvg ggtwtctaat                                                  20

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
gtgccagcmg ccgcggtaa                                                   19

<210> SEQ ID NO 7
<211> LENGTH: 20
<212> TYPE: DNA
<213> ORGANISM: Artificial Sequence -continued

```
<220> FEATURE:
<223> OTHER INFORMATION: Primer

<400> SEQUENCE: 7
ggactacvsg ggtatctaat                                            20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aatgatacgg cgaccaccga                                            20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
caagcagaag acggcatacg a                                          21
```

QUANTITATIVE SUBSTRATE UTILIZATION IN MICROBIAL ECOLOGY USING STABLE ISOTOPE PROBING

CROSS REFERENCE TO RELATED APPLICATION

This application claims priority from and benefit of U.S. Provisional Patent Application No. 62/357,266, filed on Jun. 30, 2016, the disclosure of which is incorporated herein by reference in its entirety.

STATEMENT REGARDING FEDERALLY SPONSORED RESEARCH OR DEVELOPMENT

This invention was supported by the United States Government under United States Department of Energy Grant No. DE-SC0010579. The Government has certain rights in the invention.

FIELD OF THE INVENTION

This disclosure relates to methods for quantitatively measuring substrate utilization in microorganisms using stable isotope probing technology.

BACKGROUND

The types of organisms present in an ecosystem profoundly influence its functioning, an idea well established for plants and animals, formalized in the state factor theory of ecosystem science, and illustrated through the impacts of plant and animal invasions on ecosystem processes. The physiological and taxonomic diversity of microorganisms far exceeds that of plants and animals combined. Yet, despite progress in applying molecular tools to analyze the microbial diversity of intact assemblages, the understanding of how individual microbial taxa affect ecosystem processes like element cycling remains weak. When applied to intact microbial assemblages, stable isotope probing (SIP) partly addresses this challenge, in that it physically links the fluxes of elements to an organism's genome.

Stable isotope probing (SIP) is a powerful technique for linking the genetic identity of microorganisms with their biogeochemical functioning in the environment. This is because the technique takes advantage of the particular biomolecules, namely, nucleic acids, where genetic identity and elemental composition (biogeochemistry) are literally physically connected. It is difficult to imagine a more incisive concept for linking element fluxes with genetic identity than a technique that monitors the uptake of traceable isotopes of elements into the molecules that record the genetic identity of organisms.

However, as developed and as practiced to date, the SIP technique is qualitative and does not provide quantitative measures of assimilation rates. Instead, SIP is only capable of differentiating between organisms that utilize a substrate versus those that do not. The distinction between labeled and unlabeled organisms is binary, defined by the density regions selected by the investigator, and thereby limiting the resolution of taxon-specific responses to labeled or unlabeled. The distribution of DNA along the density gradient reflects the influences of both isotope incorporation and GC (guanine-plus-cytosine) content, because the density of DNA increases with its GC content. Any comparison of density regions will reflect both influences, challenging inferences about quantitative isotope incorporation.

In conventional SIP, there are no assurances that the identification of the labeled community is complete. Low-GC-content organisms that incorporate the isotope label may not have shifted sufficiently in density to be part of the labeled density fraction, and high-GC-content organisms that do not incorporate the label may be erroneously inferred to be part of the labeled community. This could result in incomplete coverage when discrete, noncontiguous density intervals representing heavy and light fractions are selected for sequencing, omitting information about the microbial assemblage contained in the DNA at intermediate densities. Only the heavy fractions in both labeled and unlabeled treatments are sequenced and compared: any new organisms that appeared in the heavy fraction of the labeled treatment are inferred to have taken up enough of the isotope tracer to have shifted the density of their DNA. This approach could have excluded organisms that incorporated the isotope tracer but, because of their low GC content, do not shift sufficiently to be represented in the heavy fraction. In these ways. SIP as typically practiced is a qualitative technique capable of identifying some of the organisms that utilize a substrate and not a quantitative one capable of exploring the full range of variation in isotope incorporation among microbial taxa.

SUMMARY

The embodiments described herein relates to methods modifying conventional SIP so that isotopic incorporation into the genomes of individual taxa of microorganism can be quantified. Further, the embodiments disclose methods to quantify the baseline densities of the DNA of individual taxa of microorganism without exposure to isotope tracers and then to quantify the change in DNA density of each taxon caused by isotope incorporation.

In one embodiment, the microorganism is derived from soil incubation. In another embodiment, the microorganism is a bacterium.

In one embodiment, isotopically labeled substrates are derived from either $^{18}$O-enriched water (H2O), $^{13}$C-enriched glucose ($C_6H_{12}O_6$), and $^{15}$N-enriched ammonium chloride ($NH_4Cl$) or any combination of the isotopically labeled substrates.

In one embodiment, a proportional abundance of an individual taxon of the microorganism is determined by sequencing, and the density changes between the density of an individual taxon of the microorganism in unlabeled fraction and the density of the same taxon of the microorganism in the corresponding labeled fraction are separated from density changes resulted from different GC content.

In one embodiment, the density difference between two adjacent DNA density fractions is from about 0.0034 to about 0.0042 $g/cm^3$. In another embodiment the density difference between any two adjacent said fractions is about 0.0036 $g/cm^3$. In yet a further embodiment, the density difference between any two adjacent said fractions is about 0.0012 $g/cm^3$. In still a further embodiment, the density difference between any two adjacent said fractions is about 0.00012 $g/cm^3$.

In one embodiment, one can recover about 5 to 75 density fractions. In another embodiment, one can recover up to 20 density fractions. In yet a further embodiment, one can recover about 9 to 15 density fractions.

Using a model of isotope substitution in DNA, one can convert the observed change in density to isotope composition. One shows how qSIP applies in soil incubations using a specific carbon source ($^{13}$C glucose) and using a universal substrate for growing organisms ($^{18}$O water). One also shows how combining these tracers provides insight into the microbial ecology of a biogeochemical phenomenon widely observed in soil, called the "priming effect". The priming effect is the phenomenon where extra decomposition of native soil organic matter in a soil receiving an organic amendment occurs.

The opposite can also be found, where the addition of substrate suppresses organic matter mineralization. Some hypotheses to explain priming invoke microbial biodiversity, and yet, those controls remain cryptic, in part because of the difficulty of identifying organisms that respond indirectly to the addition of substrate by increasing the decomposition of native soil organic matter. Quantitative SIP has the potential to address these phenomena, by parsing out the contributions of specific microorganisms to the decomposition of the added substrate, labeled with $^{13}C$, and to the decomposition of native soil organic matter, which an $^{18}O$ water label can detect. In this way, the potential of qSIP to advance microbial ecology as a quantitative field relating microbial biodiversity to element cycling at the ecosystem scale is illustrated.

BRIEF DESCRIPTION OF THE FIGURES

FIGS. 3A-3C illustrate the relative levels of abundance of bacterial 16S rRNA genes, measured through quantitative PCR, as a function of density of DNA. Data for isotope treatments are shown with filled symbols, while data for natural abundance controls are shown with open symbols. Comparison of soil samples incubated with natural abundance glucose and $^{13}C$ glucose (A), natural abundance water and $^{18}O$ water (B), and natural abundance water plus natural abundance glucose and $^{18}O$ water plus natural abundance glucose (C);

FIGS. 4A-4F illustrate the frequency distribution of the 16S rRNA gene as a function of density of DNA for three bacterial taxa without added glucose (left) and with added (natural abundance $^{13}C$) glucose (right), the three different taxa included unidentified genera in the families Micrococcaceae (A and B) and Pseudonocardiaceae (C and D) and the genus *Herpetoszphonales* (E and F). Open symbols and dashed lines show the density distribution for the incubation where all substrates had natural abundance Isotope composition, and filled symbols and solid lines show the distribution with $^{18}O$ water. Different shapes represent individual replicates within a treatment combination;

FIG. 8 illustrates the density of DNA for taxa exhibiting or not exhibiting tracer assimilation in the three tracer experiments;

FIGS. 10A and 10B: Principal coordinates analysis (PCoA) of bacterial community structure (A) and variation in EAF 13C with the change in 18O assimilation because of glucose (B) in response to single and repeated pulses of glucose. For the regression analysis, each taxon's relative abundance (% 16 S rRNA gene sequences) and taxonomy are indicated using size and color, respectively. The dashed line and coefficient of determination show the results of a regression weighted by relative abundance (% of 16S rRNA gene sequences);

FIGS. 12A and 12B: A. Proportion of total DNA as a function of density in the $H_2^{16}O$ (o) and $H_2^{18}O$ (•) treatments. Each point represents the fractions within a 0.005 g density increment. Errors bars represent standard errors of the DNA concentration in the fractions. The density of DNA in the $H_2^{18}O$ treatments was higher than the density of DNA from the $H_2^{16}O$ controls (1524.29, p50.01). B. Fraction of 16S rRNA genes as a function of density for *Desulfovibrio mexicanus* in the $H_2^{16}O$ (o) and $H_2^{18}O$ (.) treatments. The different shapes represent individual replicates from the same SIP spin. Average density and standard error of the labeled and unlabeled DNA are shown;

DETAILED DESCRIPTION

Figure 1:
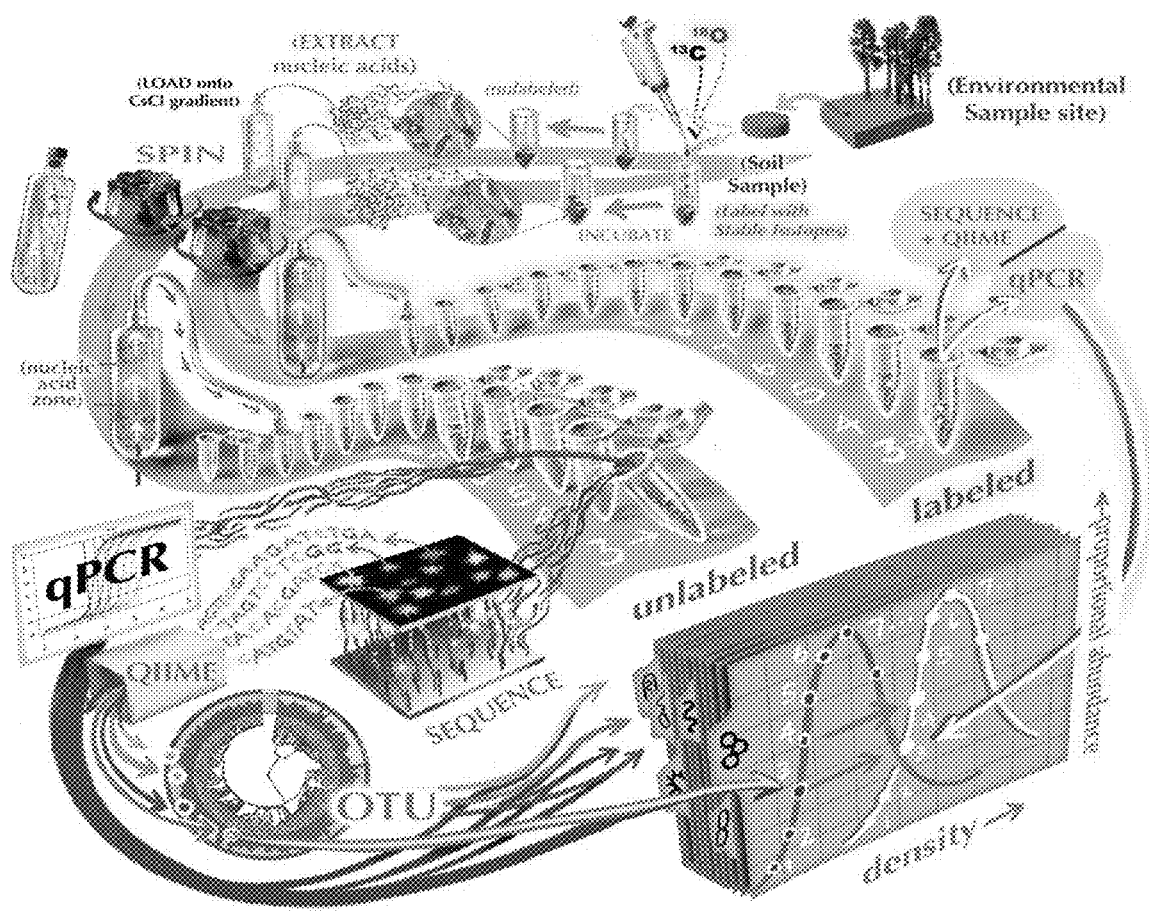
FIG. 1 illustrates a schematic of a conceptual model of the quantitative stable isotope probing technique, from sample collection to determining the density of 16S rRNA gene fractions for individual taxa and their corresponding values of atom % stable isotope composition.

The embodiments in the following description are described with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology. Thus, appearances of the phrases "in one embodiment," "in an embodiment," and similar language throughout this specification may, but do not necessarily, all refer to the same embodiment.

The described features, structures, or characteristics of the embodiments herein may be combined in any suitable manner in one or more embodiments. In the following description, numerous specific details are recited to provide a thorough understanding of embodiments. One skilled in the relevant art will recognize, however, that the embodiments herein may be practiced without one or more of the specific details, or with other methods, components, materials, and so forth. In other instances, well-known structures, materials, or operations are not shown or described in detail to avoid obscuring aspects of the described embodiment.

Making SIP quantitative (qSIP) replaces a "yes" "no" answer with a continuous quantitative response variable, which offers more sensitivity and supports exploring more nuanced, quantitative variation among microbial taxa. Further, qSIP does more than this, because the quantitative theory of isotope tracers expands the scope of possible inferences, from the movements of labeled elements in the environment, to the total fluxes of elements, to quantitative metrics of biogeochemical and ecological interest, like growth and per capita interactions among species.

Moving from a qualitative to a quantitative framework for the SIP technique also removes the subjectivity inherent in the technique as currently practiced, and offers a platform for the development of rigorous, quantitative, standards, supporting both cross-laboratory comparison, and operating the technique on a larger scale than currently possible.

SIP of bacterial assemblages in natural environments can yield quantitative information about the assimilation of isotope tracers into bacterial DNA with fine taxonomic resolution. The current disclosure establishes a framework for coupling quantitative interpretation of stable isotope tracer experiments with microbial diversity, a coupling essential for understanding how to represent microbial diversity in biogeochemical models.

qSIP also has advantages over many other techniques in taxonomic resolution. For compound-specific biomarkers, specific fatty acids serve as biomarkers for up to a dozen groups of microorganisms, which is much coarser taxonomic resolution than that afforded by qSIP. Chip-SIP requires nucleic acid probes, necessitating a priori decisions as to what sequences to collect for isotopic analysis and the preparation of microarrays implanted with those sequences prior to the addition of the isotope. For this reason, in Chip-SIP, the taxonomic resolution in the isotope fluxes is influenced by information gathered without knowledge of which taxa are biogeochemically important. One advantage of qSIP is that sequencing occurs after isotope enrichment, enabling quantitative exploration of the biodiversity involved in biogeochemistry without having to decide a priori where to focus. Furthermore, the taxonomic resolution possible with a microarray is limited by probe specificity and fidelity, whereas the resolution afforded by qSIP is very high, equivalent to the resolution of the sequencing technology applied to the density fractions. Chip-SIP also requires access to Nano-SIMS, which is expensive and technically challenging, limiting its wide adoption in the field.

Furthermore, other approaches used to link element fluxes to microbial taxa are limited to target organisms, such as fluorescent in situ hybridization (FISH) coupled with SIMS or halogen in situ hybridization-SIMS. Bromodeoxyuridine (BrdU) uptake has been proposed as a universal technique for identifying growing organisms and their responses to environmental perturbations. However, there is up to 10-fold variation among taxa in the conversion between BrdU uptake and growth that is unrelated to taxonomic affiliation, a bias calling into question the quantitative universality of this technique. Compared to these other techniques, qSIP can assess quantitatively the entire microbial assemblage at fine taxonomic resolution, a solid foundation for exploring quantitatively the relationships between microbial biodiversity and the biogeochemistry known to be microbial.

Figure 2A:
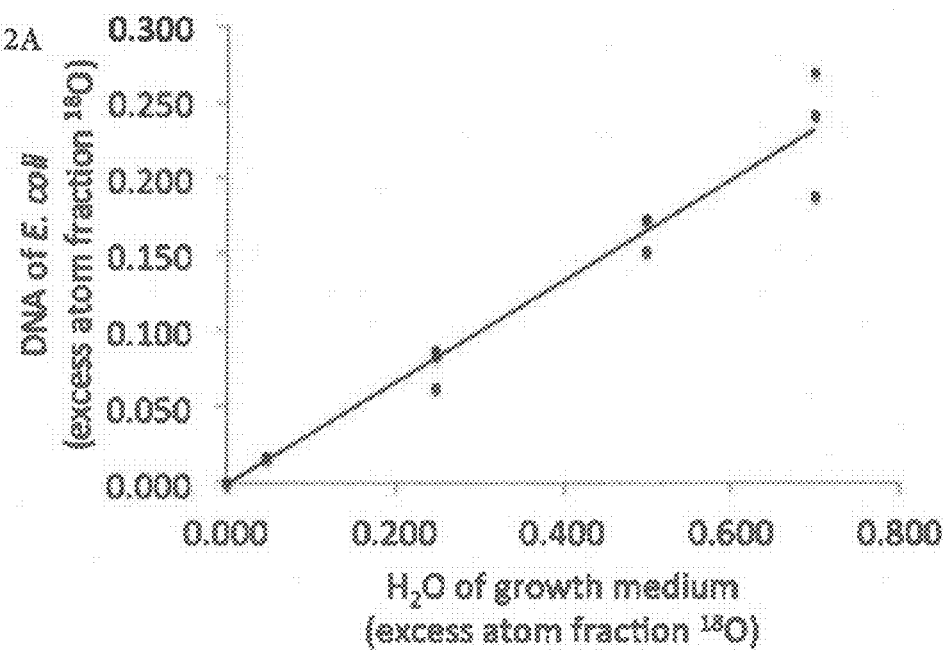
FIG. 2A is $^{18}O$ composition of *E. coli* DNA as a function of the $^{18}O$ composition of water in the growth medium.
Figure 2B:
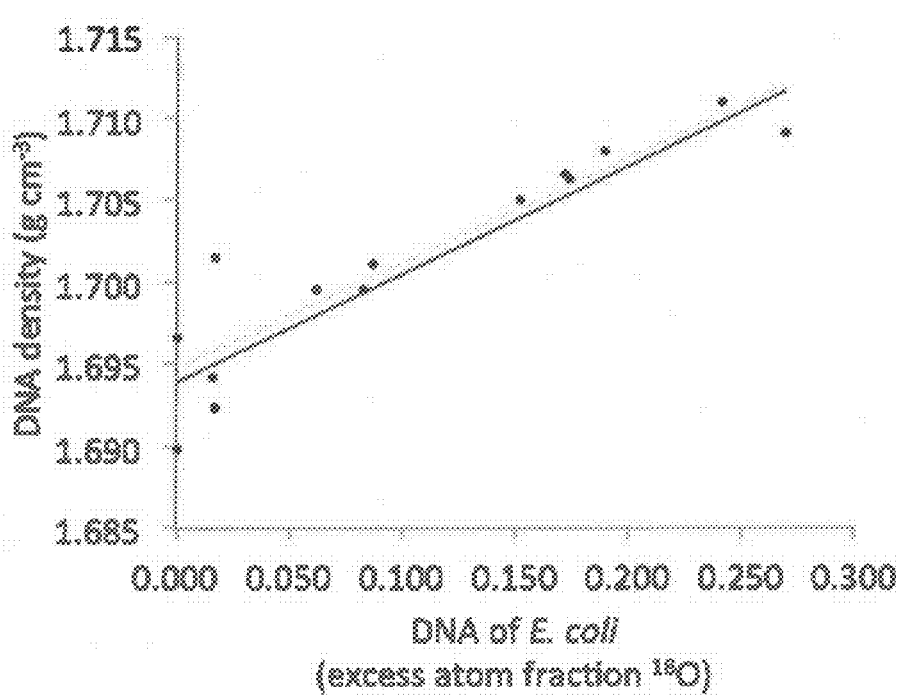
FIG. 2B is average density of *E. coli* DNA as a function of the $^{18}O$ composition of the DNA (density=0.0644×atom fraction $^{18}O$+1.6946; $R^2$=0.852; n=15)

Referring to FIGS. 2A and 2B, in certain embodiments, the predicted relationship between density and atom fraction excess is verified and ultracentrifugation in CsCl can serve as a quantitative mass separation procedure, which resolves variations in isotope tracer incorporation into DNA. In certain embodiments, the $^{18}$O composition of *E. coli* DNA was strongly related to the $^{18}$O composition of water in the growth medium, supporting the notion that oxygen from water is quantitatively incorporated into the DNA of growing organisms (P<0.001; r$^2$=0.976) (FIG. 2A). In certain embodiments, the slope of the relationship, 0.334±0.017 (mean±standard deviation; n=15), indicates that 33% of oxygen in *E. coli* DNA is derived from water. The shift in density of *E. coli* DNA with $^{18}$O incorporation matches well the theoretical prediction of the model of isotope substitution in the DNA molecule (FIG. 2B).

In certain embodiments, in soil incubations, DNA density averaged across the entire community tends to increase in response to isotope addition (FIGS. 3A-3C). Moreover, the addition of $^{13}C$ glucose (FIG. 3A) increases the density of DNA by 0.0043 g/cm$^3$, but the 90% CI for this increase overlaps zero (−0.002 to 0.0091 g/cm$^3$). In certain embodiments, the addition of $^{18}O$ water (FIG. 3B) causes a similar increase in density, 0.0041 g/cm$^3$, but the 90% CI for this increase also overlaps zero, spanning −0.0011 to 0.0090 g/cm$^3$. The incubations receiving $^{18}O$ water and supplemental glucose (natural abundance isotope composition) exhibit the largest increase in average DNA density, 0.0090 g/cm$^3$, and in this disclosure, the 90% confidence limit does not overlap zero (0.0065 to 0.0125 g/cm$^3$). These comparisons estimate the change in density of DNA fragments encoding the 16S rRNA gene across all taxa considered together. FIGS. 3A-3B also illustrate the density distributions often used in SIP experiments to visualize the qualitative cutoff between labeled and unlabeled regions suitable for sequencing.

Sequencing all fractions allowed analogous density distributions for individual taxa to be visualized. Referring to FIGS. 4A-4F, three taxa are used to illustrate the concept, showing graphically the manner in which the density of labeled ($W_{LAB_i}$) and unlabeled ($W_{LIGHT_i}$) DNA is calculated for each taxon. For example, the density of an unidentified genus in the family Micrococcaceae does not change with the addition of $^{18}O$ water in the absence of supplemental glucose.

Referring to FIG. 4A, for family Micrococcaceae, the shift in density (Z) due to $^{18}O$ incorporation is −0.0002 g/cm$^3$, with the 90% CI spanning −0.0046 to 0.0049 g/cm$^3$. Referring to FIG. 4B, the shift in density due to $^{18}O$ incorporation increases when unlabeled glucose is also added (Z=0.0169 g/cm$^3$, 90% CI of 0.0146 to 0.0194 g/cm$^3$). In certain embodiments, the bacteria family Micrococcaceae does not incorporate the $^{18}O$ tracer in unamended soil but does synthesize new DNA using $^{18}O$ derived from $H_2O$ in response to glucose addition.

Referring to FIGS. 4C and 4D, the DNA of an unidentified genus in the family Pseudonocardiaceae similarly exhibits no change in density in the absence of supplemental glucose (Z=0.0005 g/cm$^3$, 90% CI of −0.0033 to 0.0045 g/cm$^3$) and exhibits only a slight increase in response to the addition of glucose (Z=0.0040 g/cm$^3$, 90% CI of 0.0015 to 0.0070 g/cm$^3$).

The density of DNA in a member of the genus Herpetosiphonales increases in soil without any supplemental glucose (Z=0.0124 g/cm$^3$, 90% CI of 0.0105 to 0.0143 g/cm$^3$) (FIG. 4E), but the density does not increase further in response to the addition of glucose (Z=0.0110 g/cm$^3$, 90% CI of 0.0088 to 0.0133 g/cm$^3$) (FIG. 4F). Referring to FIGS. 4E and 4F, by dividing the density gradient into multiple fractions and sequencing each separately, the changes in the density of DNA for individual taxa caused by the assimilation of stable isotope tracers can be determined.

Figure 5:
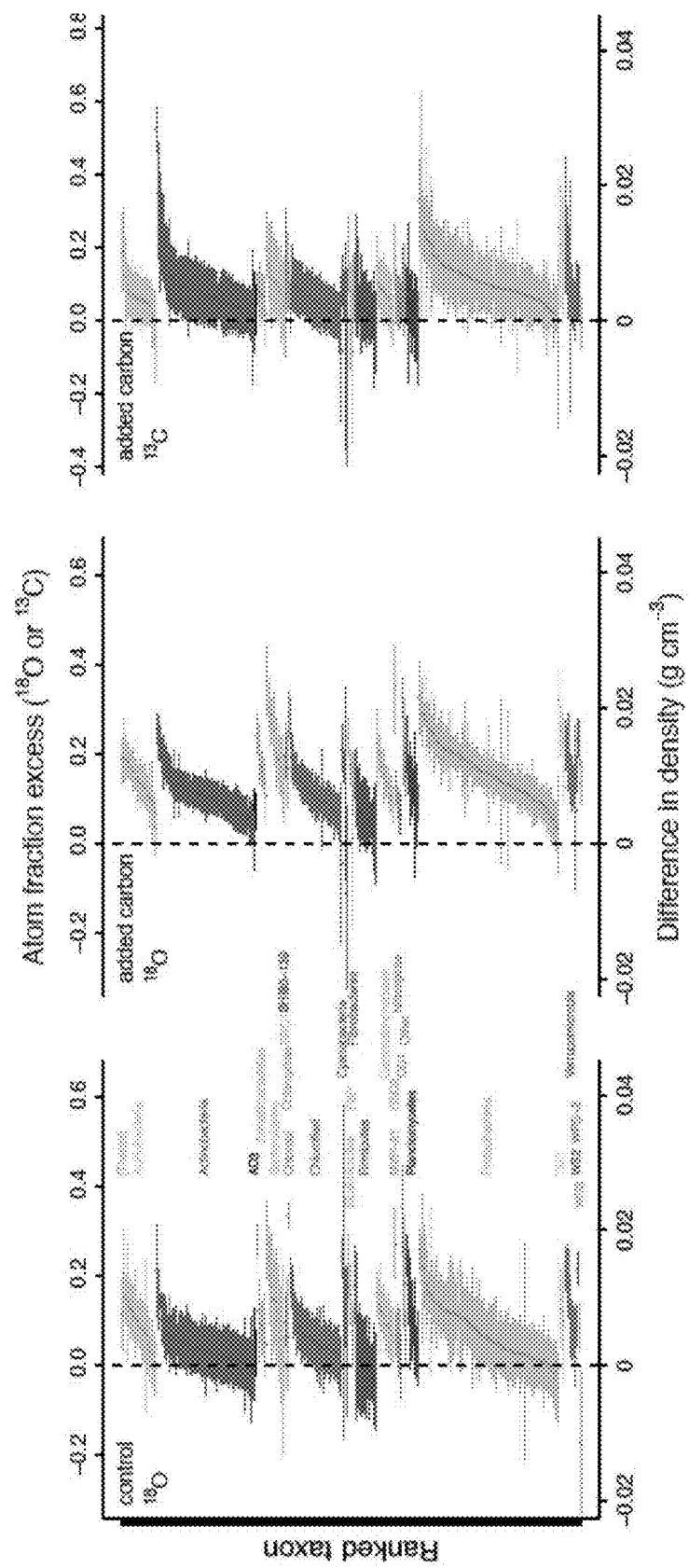
FIG. 5 illustrates taxon-specific shifts in average density of DNA (g/cm$^3$, bottom horizontal axis) and corresponding atom fraction excess of $^{18}O$ or $^{13}C$ (top horizontal axis) between incubations with enriched and natural abundance substrates. Changes in DNA density are caused by $^{18}O$ incorporation from water without (left) or with (middle) added natural abundance glucose or by $^{13}C$ incorporation from added $^{13}C$-labeled glucose (right)

Referring to FIG. 5, the taxon-specific shifts in average density associated with incorporation of the heavy isotope translate directly to quantitative variation in isotope composition, express herein as atom fraction excess $^{18}O$ ($A_{OXYGEN}$) (FIG. 5, left and middle panels) and $^{13}C$ ($A_{CARBON}$) (FIG. 5, right panel). The approach presented here achieves higher resolution by accounting for taxonomic differences in the density of DNA caused by natural variation in GC content.

In certain embodiments, the shifts in density that can be detected using qSIP in the current disclosure range from 0.0034 to 0.0042 g/cm$^3$ (FIG. 5). The value of shifts in density are nearly an order of magnitude smaller than those typically used to resolve the assimilation of stable isotopes into newly synthesized DNA using conventional SIP, in which light and heavy density fractions often differ by 0.03 g/cm$^3$ or more. For $^{13}C$, the minimum required change in density for SIP has been estimated to be 0.01 g/cm$^3$, corresponding to 0.2 atom fraction excess.

In certain embodiments, fractions in discrete density increments of 0.0036 g/cm$^3$ (average difference in density between adjacent fractions) are collected. This difference in density between the adjacent fractions collected is comparable to the density shifts of bacterial taxa that could be resolved: the mean density shift required for the lower confidence limit to exceed zero was, on average, 0.0034 g/cm$^3$ for $^{18}O$ and 0.0042 g/cm$^3$ for $^{13}C$. Thus, it is possible that separation of the nucleic acids into finer density fractions will afford higher precision in the estimates of stable isotope composition. In some embodiments, the density difference between any two adjacent said fractions of about 0.0012 g/cm$^3$ can be achieved. In some other embodiments, the density difference between any two adjacent said fractions of about 0.00012 g/cm$^3$ can be achieved.

In certain embodiments, the detection limit for a shift in density is the median change in density required to shift the lower bound of the bootstrapped 90% confidence limit above zero. The values of detection limits for a shift in density are 0.0037 g/cm$^3$ for $^{18}O$ incorporation and 0.0044 g/cm$^3$ for $^{13}C$ incorporation, changes that correspond to 0.056 atom fraction excess $^{18}O$ and 0.081 atom fraction excess $^{13}C$. No taxon exhibited a detectable decline in density in response to isotope addition (i.e., a negative mean density shift with a confidence interval that does not include zero).

In certain embodiments, more than half of the bacterial genera, about 209 genera, do not exhibit any detectable excess 80 enrichment under control conditions without added glucose; in other words, the lower bounds of the confidence intervals for these genera overlap zero (FIG. 5, left panel). In other experiments, 170 taxa do exhibit detectable $^{18}O$ enrichment without added glucose, the corresponding values of atom fraction excess $^{18}O$ ranged from 0.047 (90% CI of 0.001 to 0.100) in a member of the genus Lentzea to 0.354 (90% CI of 0.248 to 0.449) in an unidentified representative of the candidate bacterial phylum ODI. With added glucose, 351 of the 379 taxa exhibit positive atom fraction excess $^{18}O$ (90% CIs do not overlap zero), averaging 0.147 (FIG. 5, middle), with a minimum of 0.036 (90%6 CI of 0.004 to 0.064) in an unidentified genus of the family Ktedonobacteraceae and a maximum of 0.365 (90% CI of 0.282 to 0.449) in an unidentified genus within the class AT12OctB3 of the phylum Bacteroidetes.

The bacterial taxa in the soil from the current disclosure vary in atom fraction excess $^{18}O$ under control conditions and in response to added glucose (FIG. 5, left and middle panels). Atom fraction excess $^{13}C$ reflects direct assimilation of C from the added glucose (FIG. 5, right panel). Atom fraction excess $^{13}C$ ranges from no detectable enrichment among 215 of the 379 genera to over half of the carbon atoms comprising $^{13}C$ in the DNA of a member of the Micrococcaceae (0.525, 90% CI of 0.458 to 0.592).

Referring to FIG. 5, right panel, the effect of added glucose is apparent as (i) an overall stimulation of growth, independent of the specific carbon substrate, and (ii) a stimulation of growth that relied directly on glucose-derived carbon. Atom fraction excess $^{13}C$ in response to $^{13}C$ glucose addition traces the incorporation of carbon atoms from glucose (or derived from glucose via other metabolites) into newly synthesized DNA. This is expected, because the addition of glucose stimulates growth and DNA synthesis.

Referring to FIG. 8, there is no evidence of GC bias in qSIP in the current disclosure. In some experiments, negligible differences in densities exist between organisms exhibiting tracer assimilation and those not exhibiting tracer assimilation. The inferred GC contents average 52.3% (90% CI of 44.6 to 57.3) for organisms exhibiting tracer assimilation, very close to the average of 52.8% inferred GC content for taxa for which assimilation is not detected (90% CI of 45.1 to 58.2).

Figure 6:
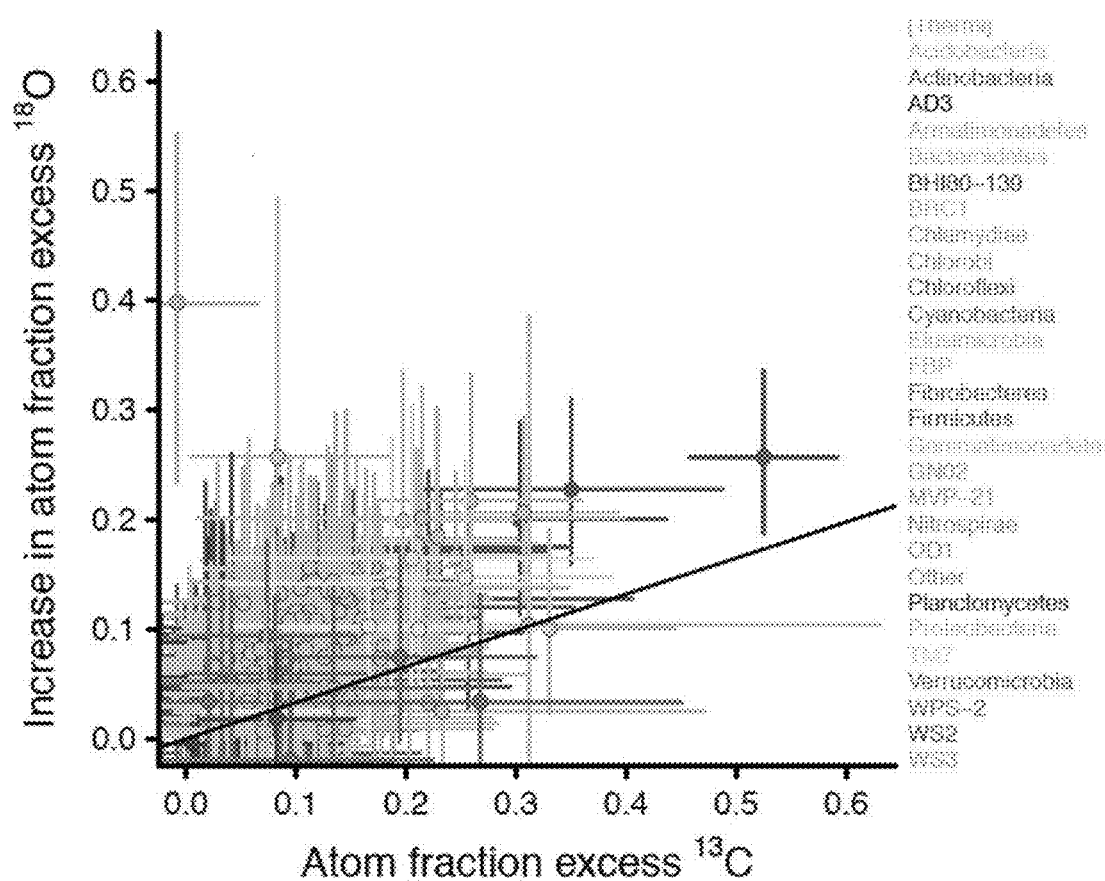
FIG. 6 shows the atom fraction $^{13}C$ with added $^{13}C$ glucose and the shift in atom fraction $^{18}O$ caused by added natural abundance glucose across groups of bacteria (n=3)
Figure 7:
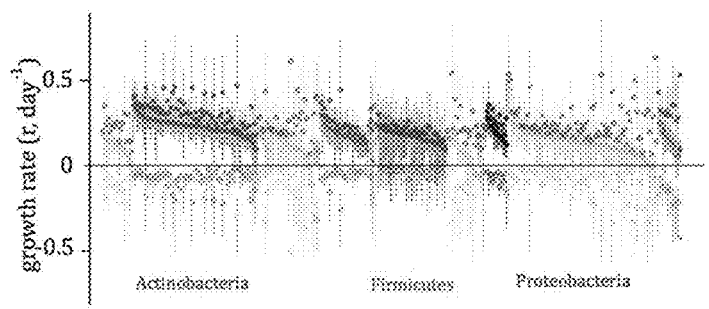
FIG. 7 illustrates the growth rate inferred from $^{18}O$—$H_2O$ incorporation in soil bacteria. Each symbol represents one taxon at the level of genus. Darker grey circles are death rates, colored circles are birth rates, and open circles are net growth (and are negative when death>birth) Each color indicates one bacterial phylum (Three are labeled as examples, the Actinobacteria, Firmicutes, and Proteobacteria)

Referring to FIG. 6, a strong positive relationship exists between increased atom fraction excess $^{18}O$ in response to the addition of glucose and the direct utilization of glucose-derived carbon (atom fraction excess $^{13}C$; $r^2=0.51$, $P<0.001$). The solid line in FIG. 6 indicates the expected relationship where glucose is the sole carbon source, and thus, there should be a 0.33 atom fraction excess increase in $^{18}O$ for each 1 atom fraction excess increase in $^{13}C$, based on the finding that 33% of the oxygen molecules in DNA are derived from water (FIG. 2). For many taxa, the increase in atom fraction excess $^{18}O$ in response to added glucose exceeded the expected amount (FIG. 6, solid line).

Although the embodiments are described in considerable detail with reference to certain methods and materials, one skilled in the art will appreciate that the disclosure herein can be practiced by other than the described embodiments, which have been presented for purposes of illustration and not of limitation. Therefore, the scope of the appended claims should not be limited to the description of the embodiments contained herein.

EXAMPLES

Example 1—Soil Incubations and DNA Extractions

The sample processing scheme, from soil collection, nucleic acid extraction, and centrifugation to data analysis, is summarized in FIG. 1. Soil (0 to 15 cm) was collected in November 2012 from a *ponderosa* pine forest meadow, located on the C. Hart Merriam Elevation Gradient in northern Arizona (35.42° N, 111.67° W; nau.edu/ecoss/what-we-do/future-ecosystems/elevation-gradient-experiment/). Soil was sieved (2-mm mesh), left to air dry for 96 h, and then stored at 4° C. before the experiment started. Amounts of 1 g of soil were added to 15-ml Falcon tubes and adjusted to 60% water holding capacity, incubated for 1 week, and then allowed to air dry for 48 h prior to the addition of isotopes. Samples were incubated for 7 days.

During the incubation, samples received 200 μl of water per gram of soil or a glucose solution at a concentration of 500 μg C/g soil in the following isotope and substrate treatments (n=3 for each): treatment 1, water at natural abundance $\delta^{18}O$; treatment 2, $^{18}O$-enriched water (atom fraction 97%); treatment 3, glucose and water at natural abundance $\delta^{13}C$ and $\delta^{18}O$; treatment 4, $^{13}C$-enriched glucose (atom fraction 99%) and water at natural abundance $\delta^{18}O$; and treatment 5, glucose at natural abundance $\delta^{13}C$ and $^{18}O$-enriched water (atom fraction 97%). These treatments were selected in order to evaluate the effects of isotope addition on the density and isotopic composition of DNA. The following effects were assessed: (i) the effect of $^{18}O$ in the absence of supplemental glucose as the difference between treatments 2 and 1, (ii) the effect of $^{13}C$ in the presence of supplemental glucose as the difference between treatments 4 and 3, and (iii) the effect of $^{18}O$ with supplemental glucose as the difference between treatments 5 and 3. In each case, these comparisons isolate the effect of the presence of an isotope tracer. The specific equations quantifying these comparisons are presented below.

After the incubation, samples were frozen and stored at 40° C. DNA was extracted from approximately 0.5 g soil using a FastDNA spin kit for soil (MP Biomedicals, Santa Ana, Calif., USA) following the manufacturer's directions. Extracted DNA was quantified using the Qubit double-stranded DNA (dsDNA) high-sensitivity assay kit and a Qubit 2.0 fluorometer (Invitrogen, Eugene, Oreg., USA).

Density Centrifugation and Fraction Collection

To separate DNA by density, 5 g of DNA was added to approximately 2.6 ml of a saturated CsCl and gradient buffer (200 mM Tris, 200 mM KCl, 2 mM EDTA) solution in a 3.3-ml OptiSeal ultracentrifuge tube (Beckman Coulter, Fullerton, Calif., USA). The final density of the solution was 1.73 g/cm³. The samples were spun in an Optima Max benchtop ultracentrifuge (Beckman Coulter, Fullerton, Calif., USA) using a Beckman TLN-100 rotor at 127,000 g for 72 h at 18° C. After centrifugation, the density gradient was divided into fractions of 150 l each using a fraction recovery system (Beckman Coulter, Inc., Palo Alto, Calif., USA). The density of each fraction was subsequently measured with a Reichert AR200 digital refractometer (Reichert Analytical Instruments, Depew, N.Y., USA). DNA standards of known GC content were not included in each ultracentrifuge tube. Such standards are traditionally included when computation of GC content based on density is the primary goal but are not typically included in SIP studies.

DNA was separated from the CsCl solution using isopropanol precipitation, resuspended in 50 μl sterile deionized water, and quantified for each density fraction. The total numbers of bacterial 16S rRNA gene copies were determined in each density fraction by quantitative PCR (qPCR) using a pan-bacterial broad-coverage quantitative PCR technique. All fractions were analyzed in triplicate in 10 μl reaction mixtures that included 1 μl of DNA template and 9 μl of reaction mixture containing 1.8 M forward (5'-CCTACGGGDGGCWGCA-3') (SEQ ID NO. 1) and reverse (5'-GG ACTACHVGGGTMTCTAATC-3') (SEQ ID NO. 2) primers (bold letters denote degenerate bases), 225 nM TaqMan minor groove-binding probe (6FAM [6-carboxyfluorescein] 5'-CAGCAGCCGCGGTA-3' MGBNFQ) (SEQ ID NO. 3), 1 Platinum quantitative PCR supermix-UDG (Life Technologies, Grand Island, N.Y.), and molecular-grade water. Amplification and real-time fluorescence detection were performed on the 7900HT real-time PCR system (Applied Biosystems). The qPCR data for all density fractions in the supplemental material were provided.

Data Analysis of Total 16S rRNA Gene Copy Numbers.

Based on the qPCR data, a conventional SIP density curve was produced by graphing the proportion of total 16S rRNA gene copies as a function of density, an approach often used to visualize the effect of isotope incorporation on the distribution of densities across the bacterial assemblage, delineating heavy and light regions for sequencing. The average DNA density for each tube was calculated as a weighted average of the density of each fraction in which 16S rRNA gene copies were detected, weighted by the proportional abundance of total 16S rRNA gene copies measured in that fraction for each tube. This provided an estimate of the average DNA density for each tube, enabling bootstrap testing of whether the addition of the isotope increased the density of DNA.

Sequencing 16S rRNA Genes

The 16S rRNA gene was sequenced in every density fraction that contained DNA (9 to 15 fractions per centrifuge tube) by dual-indexing amplicon-based sequencing on the Illumina MiSeq (Illumina, Inc., San Diego, Calif. USA), using a previously published method. For each density fraction, the 16S rRNA gene V3-V4 hyper-variable region was amplified in 25 µl reaction mixtures that included 5 µl of genomic DNA (gDNA) in a 20 µl reaction mixture containing 12.5 µl Phusion high-fidelity PCR master mix with HF buffer (New England BioLabs, Inc., Ipswich, Mass., USA), 0.75 µl dimethyl sulfoxide (DMSO), 1.75 µl sterile water, and 0.2 M each forward (5'-ACTC-CTACGGGAG GCAGCAG-3') (SEQ ID NO. 4) and reverse (5'-GGACTACHVGGGTWTCTAAT-3') (SEQ ID NO. 5) primers, each concatenated to a linker sequence, a 12-bp barcode, and a heterogeneity spacer of 0 to 7 bp in size. The following thermocycling conditions were used: an initial denaturation at 98° C. for 30 s, followed by 30 cycles of denaturation at 98° C. for 30 s, annealing at 62° C. for 30 s, and amplification/extension at 72° C. for 30 s. The resultant amplicons were normalized and pooled using the SequelPrep normalization kit (Life Technologies, Carlsbad, Calif., USA), purified using AMPure XT beads (Beckman Coulter Genomics, Danvers, Mass., USA), and sequenced in combination with 20% PhiX control library (version 3; Illumina) in 300-bp paired-end MiSeq runs.

Data Analysis

Subsequent sequence processing and quality filtering were also performed as described in Fadrosh et al. Each read was assigned to the original sample based on the 24-bp dual-index barcode formed by concatenating the 12-bp barcodes from each paired-end read. After trimming the primer sequences, the original V3-V4 amplicon was reconstituted by stitching the paired-end reads without preliminary quality filtering using FLASH, as FLASH includes error correction. 9,378,878 high-quality stitched reads that were subsequently processed at a median length of 410 bp were obtained.

The stitched reads were clustered using the uclust-based open reference operational taxonomic unit (OTU) picking protocol described in QIIME (version 1.8.0-dev) against the Greengenes 13_8 reference database. Representative sequences for each OTU were chosen as the cluster centroid sequences. OTUs with representative sequences that could not be aligned with PyNAST and OTUs with a total count of less than 2 across all samples (i.e., singleton OTUs) were excluded from subsequent analyses, leaving a total of 76,710 OTUs composed of 9,127,632 reads.

All taxonomic assignments used throughout this study were generated by QIIME's uclust consensus taxonomy assigner (default parameters) against the Greengenes 13_8 97% reference OTUs. The taxonomic abundances for each sample-taxon combination using the uclust consensus assigner were compared with taxonomic assignments made with the RDP classifier (confidence level of 0.5) using a nonparametric Pearson correlation test with 999 iterations. For each sample-taxon combination, taxonomic abundances were compared for the two assignment methods (i.e., using QIIME's compare_taxa_summaries.py script). The resulting P values were significant (P 0.001) at all taxonomic levels, and the Pearson r values were high (0.96) (see Table S1 in the supplemental material), indicating that the taxonomic profiles generated by the different methods were nearly identical. The analyses performed here focused on taxonomic classification to the level of genus, of which the uclust consensus assignment yielded a total of 790 genera. The genera included for analysis were the 379 that occurred in all replicate tubes; these were also the most abundant taxa, representing 99.531% of the total 16S rRNA gene copies across the data set. All QIIME commands used in this analysis are provided in the supplemental material.

Overview of Quantitative Taxon-Specific Isotope Incorporation

In the following sections, the calculations required to determine the isotopic composition of individual taxa after exposure to isotopically labeled substrates are described. In this approach, the taxon-specific density of DNA in the treatment with the isotopically labeled substrate is computed and compared to the density of DNA for the same taxon in the treatment with no added isotope tracer. For a particular element and isotope, the density of DNA will reach a maximum value % when all atoms of that element in the DNA molecule are labeled with the isotope tracer. Smaller shifts in density reflect intermediate degrees of tracer incorporation; the scaling between density shift and isotope incorporation is linear after accounting for the effect of GC content on the elemental composition of DNA. The incorporation of the isotope tracer is expressed as atom fraction excess, which is the increase above the natural abundance isotopic composition and ranges from a minimum of 0 to a maximum of 1 minus the natural abundance background for a given isotope-element combination. Variables, calculated quantities, and indices are defined in Table 1.

TABLE 1

Definitions of indices, variables, and calculated quantities used in modeling excess atom fraction $^{18}$O for each bacterial taxon.

| | Indices: |
|---|---|
| i | taxon |
| j | replicate (or tube) within a treatment |
| k | fraction (within a replicate) |
| I | number of taxa |
| J | number of replicates (within a treatment) |
| K | number of fractions (within a replicate) |
| | Variables: |
| $f_{jk}$ | total number of 16S rRNA gene copies per µL (all taxa combined) in fraction k of replicate j (copies µL$^{-1}$) |
| $p_{ijk}$ | proportion of the total number of 16S rRNA gene copies per µL that are taxon i in fraction k of replicate j (unitless) |
| $x_{jk}$ | density of fraction k of replicate j (g cm$^{-3}$) |
| | Calculated quantities: |
| $y_{ijk}$ | number of 16S rRNA gene copies per µL of taxon i in fraction k of replicate j (copies µL$^{-1}$) |
| $y_{ij}$ | total number of 16S rRNA gene copies per µL of taxon i in replicate j (copies µL$^{-1}$) |
| $W_{ij}$ | observed weighted average density for taxon i in replicate j (g cm$^{-3}$) |
| $W_{LABi}$ | mean observed weighted average density for taxon i in the labeled treatment (mean across all replicates of the treatment with the heavy isotope) (g cm$^{-3}$) |
| $W_{LIGHTi}$ | mean observed weighted average density for taxon i in the unlabeled (i.e., natural abundance) treatment (mean across all replicates in all treatments without heavy isotopes) (g cm$^{-3}$) |
| $G_i$ | guanine + cytosine content of taxon i (unitless) |
| $H_{CARBONi}$ | average number of carbon atoms per DNA nucleotide for taxon i |
| $M_{LIGHTi}$ | observed molecular weight of the DNA fragment containing the 16S RNA gene for taxon i in the unlabeled (i.e., natural abundance) treatment (g mol$^{-1}$) |
| $M_{HEAVYMAXi}$ | theoretical molecular weight of the DNA fragment containing the 16S RNA gene for taxon i assuming maximum labeling by the heavy isotope (g mol$^{-1}$) |
| $M_{LABi}$ | observed molecular weight of the DNA fragment containing the 16S RNA gene for taxon i in the labeled treatment (g mol$^{-1}$) |
| $Z_i$ | difference in observed weighted average densities of taxon i for the labeled and unlabeled treatments (g cm$^{-3}$) |
| $A_{OXYGENi}$ | excess atom fraction of $^{18}$O in the labeled versus unlabeled treatment for taxon i (unitless) |

TABLE 1-continued

Definitions of indices, variables, and calculated quantities used in modeling excess atom fraction $^{18}$O for each bacterial taxon.

$A_{CARBONi}$  excess atom fraction of $^{13}$C in the labeled versus unlabeled treatment for taxon i (unitless)

Calculating Taxon-Specific Changes in Density

Taxon-specific changes in density caused by isotope incorporation were calculated as shown in equations 1 to 12 below. Calculations at the scale of individual density fractions (equation 1) and of individual replicate tubes (equations 2 and 3) were conducted for each density fraction and each tube independently. Other calculated quantities compared tubes with and without isotopes (equations 4 and 10 to 12), where means were used across replicates to estimate the mean difference and resampling with replacement (bootstrapping) to determine confidence intervals (CIs), as described below. In all cases, the independence of true replicates was preserved.

As described above, the total number of 16S rRNA gene copies ($f_k$) were determined using the universal 16S rRNA primer for qPCR of each fraction (k) in each replicate density gradient (j). Also as described above, sequencing was used to determine the proportional abundance of each taxon (i) within each density fraction (k), again for each replicate density gradient (j). This proportional abundance of each individual taxon within an individual density gradient from a particular replicate tube is abbreviated $p_{ijk}$. The total number of 16S rRNA gene copies were calculated per 1 ($y_{ijk}$) for bacterial taxon i in density fraction k of replicate j as follows:

$$y_{ijk} = p_{ijk} \cdot f_k \qquad (1)$$

The total number of 16S rRNA gene copies ($y_{ij}$) for bacterial taxon i in replicate j is summed across all K density fractions as follows:

$$y_{ij} = \Sigma y_{ijk} \qquad (2)$$

The density ($W_{ij}$) for bacterial taxon i of replicate j was computed as a weighted average, summing across all K density fractions the density ($x_{jk}$) of each individual fraction times the total number of 16S rRNA gene copies ($y_{ijk}$) in that fraction, expressed as a proportion of the total 16S rRNA gene copies ($y_{ij}$) for taxon i in replicate j, as follows:

$$W_{ij} = \Sigma x_{jk} \cdot (y_{ijk}/y_{ij}) \qquad (3)$$

For a given taxon, the difference was calculated in density caused by isotope incorporation ($Z_i$) as follows:

$$Z_i = W_{LABi} - W_{LIGHTi} \qquad (4)$$

where $W_{LABi}$ is the mean, across all replicates, of the isotope-enriched treatment (labeled [LAB]; n=3) and $W_{LIGHTi}$ is the mean, across all replicates, of the unlabeled treatment (unlabeled [LIGHT]; n=6). Because our experiment had multiple treatments without heavy isotopes, data from all replicate tubes were included in those unlabeled treatments (i.e., unlabeled treatments with and without added carbon; n=6) to estimate the unlabeled average density ($W_{LIGHTi}$) for each taxon i.

Calculating Taxon-Specific GC Content and Molecular Weight

The GC content ($G_i$) of each bacterial taxon was calculated using the mean density for the unlabeled ($W_{LIGHTi}$) treatments (n=6). The relationship between GC content and buoyant density was derived using DNA from pure cultures of three microbial species with known and strongly differing GC contents (see below). For these cultures, the linear relationship between GC content ($G_i$, expressed as a proportion) and unlabeled buoyant density ($W_{LIGHTi}$) on a CsCl gradient was as follows:

$$G_i = 1/0.083506 \cdot (W_{LIGHTi} - 1.646057) \qquad (5)$$

This relationship differs from the established relationship between GC content and density. As noted above, our method of determining density relied on direct measurements of refraction on individual density fractions, as is the typical practice for SIP studies. It is possible that including DNA standards of known GC content in each ultracentrifuge would yield results more consistent with the established relationship. Practitioners should include specific measures to calibrate their laboratory techniques to this relationship.

The natural abundance molecular weight of DNA is a function of GC content, based on the atomic composition of the four DNA nucleotides. Single-stranded DNA made of pure adenine (A) and thymine (T) has an average molecular weight of 307.691 g/mol. The corresponding average molecular weight for DNA comprising only guanine (G) and cytosine (C) is 308.187 g/mol. When the GC content is known, the average molecular weight of a single strand of DNA can be calculated using the following equation:

$$M_{LIGHTi} = 0.496 G_i + 307.691 \qquad (6)$$

Percent Change in Molecular Weight Associated with Isotope Incorporation

There are 12 oxygen atoms per DNA nucleotide pair, regardless of GC content: 6 each for G and C, 7 for T, and 5 for A. These atoms contain $^{18}$O at natural abundance, which is assumed to be 0.002000429 atom fraction for $^{18}$O. The maximum labeling is achieved when all oxygen atoms are replaced by $^{18}$O. Therefore, given the molecular weight of each additional neutron (1.008665 g/mol), the maximal increase in molecular weight (corresponding to 1 atom fraction $^{18}$O, or 100% atom percent $^{18}$O) is 12.07747 g/mol. The theoretical maximum molecular weight ($M_{HEAVYMAXi}$) of fully $^{18}$O-labeled DNA for taxon i is then calculated as follows:

$$M_{HEAVYMAXi} = 12.07747 + M_{LIGHTi} \qquad (7)$$

In contrast, the number of carbon atoms per DNA nucleotide varies with GC content. There are 10 carbon atoms in G, A, and T but only 9 in C. The average number of carbon atoms per DNA nucleotide ($H_{CARBONi}$) for taxon i can therefore be expressed as follows:

$$H_{CARBONi} = 0.5 G_i + 10 \qquad (8)$$

These atoms are assumed to be $^{13}$C-labeled at natural abundance (0.01111233 atom fraction $^{13}$C). The maximal labeling is achieved when all carbon atoms are replaced by $^{13}$C. Complete replacement of carbon atoms with $^{13}$C increases the molecular weight by 9.974564 g/mol for G, A. and T and by 8.977107 g/mol for C. Using equation 8, the theoretical maximum molecular weight ($M_{HEAVYMAXi}$) of fully $^{13}$C-labeled DNA can be calculated as follows, with GC content ($G_i$) expressed as a proportion:

$$M_{HEAVYMAXi} = -0.4987282 G_i + 9.974564 + M_{LIGHTi} \qquad (9)$$

Calculating isotope enrichment from density shifts. One calculated the proportional increase in density ($Z_i$) relative to the density of the unlabeled treatments ($W_{LIGHTi}$) and calculated the molecular weight of DNA for taxon i in the labeled treatment ($M_{LABi}$) as follows:

$$M_{LABi} = (Z_i/W_{LIGHTi} + 1) \cdot M_{LIGHTi} \qquad (10)$$

The atom fraction excess of $^{18}O$ for taxon i ($A_{OXYGENi}$), accounting for the background fractional abundance of $^{18}O$ (0.002000429), is then calculated as follows:

$$A_{OXYGENi} = (M_{LABi} - M_{LIGHTi}/M_{HEAVYMAXi} - M_{LIGHTi}) \cdot (1 - 0.002000429) \quad (11)$$

The results from a pure culture study were used with *Escherichia coli*, grown using water with different levels of $^{18}O$ enrichment (natural abundance, 5, 25, 50, and 70% atom fraction $^{18}O$; see below) to compare to the theoretical calculations of atom fraction excess $^{18}O$ derived above.

Similarly, the atom fraction excess $^{13}C$ for taxon i ($A_{CARBONi}$), accounting for the background fractional abundance of $^{13}C$ (0.01111233), is calculated as follows:

$$A_{CARBONi} = (M_{LABi} - M_{LIGHTi}/A_{HEAVYMAXi} - M_{LIGHTi}) \cdot (1 - 0.01111233) \quad (12)$$

Example 2—Pure Culture Studies

To verify the predicted relationship between increased density and atom fraction excess, experiments were conducted with a pure *Escherichia coli* culture. The *E. coli* (strain HB101, GC content 50.8%) culture was shaken at 100 rpm for 8 h at 37° C. in Luria-Bertani (LB) broth that was prepared with a mixture of natural abundance and $^{18}O$ water to achieve five $^{18}O$ enrichment levels (natural abundance, 5, 25, 50, and 70% atom fraction $^{18}O$). Genomic DNA was extracted in triplicate using the PowerLyzer UltraClean microbial DNA isolation kit according to the manufacturer's instructions (Mo Bio Laboratories, Inc., Carlsbad, Calif.). Pure cultures of two additional strains of bacteria selected for low GC content (*Staphylococcus epidermidis* ATCC 49461, 32.1%) and high GC content (*Micrococcus luteus* ATCC 49732, 73%) were also grown. *S. epidermidis* was grown for 24 h on brain heart infusion agar at 37° C., and *M. luteus* was grown with LB agar at 23° C. These cultures were grown with substrates and water at natural abundance stable isotope composition.

For each culture, genomic DNA was extracted in triplicate. Approximately 800 ng of each DNA extract was used for isopycnic centrifugation, density quantification, and DNA isotope analysis. The $^{18}O$ composition of the *E. coli* DNA was determined with a PyroCube (Elementar Analysen-systeme GmbH, Hanau, Germany) interfaced to a PDZ Europa 20-20 isotope ratio mass spectrometer (Sercon Ltd., Cheshire, United Kingdom) at the UC Davis Stable Isotope Facility (Davis, Calif.). Samples were prepared by diluting the *E. coli* DNA with natural abundance salmon sperm DNA to achieve enrichment levels below 100% $^{18}O$ for isotope analysis. The densities of DNA from the cultures grown at natural abundance isotope composition were used to determine the relationship between the density of DNA and its GC content, yielding the relationship described in equation 5 ($r^2 = 0.912$; $P < 0.001$).

Statistical Analysis

Linear regression was used to examine the relationships between the $^{18}O$ water composition of the growth medium and the $^{18}O$ composition of *E. coli* DNA, as well as between the $^{18}O$ composition of *E. coli* DNA and its density.

Following the equations above, the difference was computed in densities, $Z_i$, between treatments with and without isotope tracers and the corresponding values of isotope composition, $A_{OXYGENi}$ and $A_{CARBONi}$. Each calculated quantity was determined for each replicate sample. One then used bootstrap resampling (with replacement, 1,000 iterations) of replicates within each treatment to estimate taxon-specific 90% CIs for the change in density (equation 4) and the corresponding value of atom fraction excess isotope composition (equation 11 for oxygen and equation 12 for carbon). For each bootstrap iteration, three samples (with replacement) were drawn from the treatment with added isotope and six samples were drawn from the no-isotope controls. All calculations were performed in R.

Density fractionation separates organisms according to GC content, as well as isotope incorporation, so traditional SIP may be biased toward identifying high-GC-content organisms as growing or utilizing a substrate. To test whether qSIP exhibited any such bias, One used density without isotope addition as a proxy for GC content and tested whether the densities of organisms identified as assimilating (90% CIs did not include 0 for $A_{CARBON}$ or $A_{OXYGEN}$) differed in density from organisms where assimilation was not detected.

The focus was on the magnitude of variation in $Z_i$, $A_{OXYGEN}$, and $A_{CARBON}$, because the goal of our work was to establish a means to discern from SIP experiments quantitative estimates of isotope tracer uptake. These values lie along a continuum from no uptake to complete isotope replacement, and our approach estimates the values and places confidence limits on those estimates. One did not use null hypothesis significance testing for assessing density shifts and isotope tracer uptake, because our priority was on estimation rather than determining statistical significance. For this reason, bootstrap resampling was selected rather than, for example, t tests or analyses of variance (ANOVAs). Parametric tests could of course be applied in future applications of this technique and may be appropriate, for example, for statistical comparisons of treatments postulated to alter isotope tracer uptake. In such cases, correcting for multiple comparisons may be appropriate, depending on the nature of the question and the balance between type I and type II error rates. One note that, in typical SIP experiments, an organism is considered to be growing or utilizing a substrate if it exhibits a change in relative abundance when comparing the heavy fraction of the labeled sample to the control or comparing the heavy fraction to the light fraction, and yet, assessments of variation in these estimates are not typically presented. Our approach assesses both the quantitative values of isotope uptake and the variation associated with those estimates.

Accession number. All sequence data have been deposited at MG-RAST under project accession number 14151.

The combination of $^{18}O$ and $^{13}C$ tracers enabled quantitative partitioning of these direct and indirect effects, based on the deviation in the data from the expected relationship between $^{18}O$ and $^{13}C$ enrichment for organisms utilizing glucose as a sole carbon source (solid line, FIG. 6). An explanation of the deviation observed is that it represents the utilization of C sources other than glucose for growth. In other words, the added glucose stimulated the utilization of native soil C as a growth substrate. This points to the potential for quantitative stable isotope probing to test hypotheses regarding microbial diversity in the commonly observed phenomenon where the addition of simple C substrates to soil alters the mineralization of native soil C. Combining isotope tracers (using both $^{13}C$ and $^{18}O$) can help by distinguishing microorganisms that respond to the original substrate pulse from those that respond indirectly by degrading soil organic matter, an approach useful for testing hypotheses about which groups of microorganisms contribute to priming. qSIP advances this one step further, by enabling quantitative comparisons of microorganisms' utilization of the added substrate and of soil organic matter for growth.

Future analyses combining qSIP with system-level C fluxes would support stronger inferences about the role of specific microorganisms in the priming effect. The analysis presented here suggests that some microorganisms respond to glucose addition by enhancing their rates of utilization of native soil carbon, enabling additional biosynthesis (FIG. 6). More generally, the taxonomic diversity of responses highlights the potential for this technique to provide insight into the population and community ecology behind biogeochemical phenomena involving such indirect effects.

Example 3—Bacterial Carbon Use Plasticity, Phylogenetic Diversity and the Priming of Soil Organic Matter Materials and Methods Soil (0-15 cm) was collected from a ponderosa pine meadow (35.41541N, −111.6695W, 2344 m elevation), vegetated with patches of grass on the C. Hart Merriam elevation gradient in November 2012. Soil from this site was previously determined to be a Sponseller clay loam with 36.1% clay, 43.5% silt and 20.4% sand. This soil was also characterized as having 2.6±0.1% C content, 0.12±0.01% N content (Dijkstra P, Ishizu A, Doucett R, Hart S C, Schwartz E, Menyailo O V et al. (2006). $^{13}$C and $^{15}$N natural abundance of the soil microbial biomass. *Soil Biol Biochem* 38: 3257-3266) and a relatively neutral pH of 6.8. Soil was sieved through 2 mm mesh, and air-dried at room temperature for ~24 h before initiation of the experiment. Soils were dried to enable the addition of isotopically labeled solutions without saturating the soil.

To quantify priming, 40 g dry weight soil was weighed into specimen cups, brought up to 60% water holding capacity and placed in 32 oz mason jars (946.3 ml) with septa in the lids to pre-incubate for 7 days. Following this, half of the jars (n=5) received 500 μg C per g soil in 125 μl of a uniformly labeled $^{13}$C-glucose solution (992‰), whereas the other half received the same amount of deionized water to serve as a non-amended control. These additions were repeated weekly for 6 weeks with the incubation terminating the end of week 6. As root exudation rates in forests can range from ~200 μg to 3000 μg C per g root per week (for example, Phillips R P, Finzi A C, Bernhardt E S. (2011). Enhanced root exudation induces microbial feedbacks to N cycling in a pine forest under long-term $CO_2$ fumigation. *Ecol Lett* 14: 187-194; Yin H, Wheeler E, Phillips R P. (2014). Root-induced changes in nutrient cycling in forests depend on exudation rates. *Soil Biol Biochem* 78: 213-221.) our amendment simulated a realistic C flux to root-associated soil. Headspace gas samples for $CO_2$ concentration and $\delta^{13}$C were taken three and four times a week in the control and glucose-amended samples, respectively. Following gas sampling, incubations were left uncovered for ~30 min to allow gas exchange, refreshing $O_2$ and preventing $CO_2$ saturation. Glucose and soil organic matter-derived $CO_2$—C was partitioned in the glucose-amended samples using mass balance:

$$C_{SOC}=C_{total}(\delta_{total}-\delta_{glucose})/(\delta_{SOC}-\delta_{glucose})$$

where $C_{SOC}$ is $CO_2$—C from native SOC (μg C per g soil), $C_{total}$ is measured $CO_2$—C from glucose-amended samples (μg C per g soil). $\delta_{total}$ is the measured $\delta^{13}$C signature of $CO_2$ from glucose-amended samples, $\delta_{glucose}$ is the $\delta^{13}$C signature of the glucose solution (992‰) and $\delta_{SOC}$ is the average $\delta^{13}$C signature from the native SOC measured from the non-amended samples. Priming was calculated as the difference between SOC oxidation of the amended and non-amended samples and reported as $CO_2$—C μg per g soil.

Owing to the expense associated with isotopically labeled substrates, stable isotope probing was conducted in parallel incubations that had less soil and were in smaller containers but were otherwise treated identically to the gas flux incubations described in Examples 1 and 2. Although these differences in incubation conditions could affect headspace $O_2$ and $CO_2$ concentrations, we expect these difference to be relatively small because the containers where opened regularly and allowed to exchange with the atmosphere. Briefly, 1 g dry weight soil was weighed into 15 ml Falcon tubes. In week 1, half the samples (n=18) received one of six isotope combinations (n=3): $^{16}$O-water only, $^{18}$O-water only, $^{12}$C-glucose+$^{16}$O-water, $^{13}$C-glucose+$^{16}$O-water, $^{12}$C-glucose+$^{18}$O-water. The $^{13}$C-glucose was at atom fraction 99% and the $^{18}$O-water was atom fraction 97%. The other half received unlabeled water or glucose weekly until week 6, when they received one of the above isotope treatments. As with the gas flux incubations, samples were adjusted to 60% water holding capacity and received either 500 μg C per g soil or an equivalent volume of water each week. Samples were incubated with the isotope treatment for 7 days before being frozen at −80° C. DNA was then extracted using the MP Biomedicals FastDNA spin kit (Solon, Ohio, USA). Ultracentrifugation, fractionation, quantitative PCR and sequencing were conducted as described in Examples land 2. Briefly, 5 μg of DNA per sample was separated on a CsCl density gradient via ultracentrifugation at 127 000 g for 72 h at 18° C. using a TLN-100 Rotor in a Optima Max bench top ultracentrifuge (Beckman Coulter, Fullerton, Calif., USA). Density fractions (~150 μl) were collected and DNA was purified using isopropanol precipitation. Bacterial 16S ribosomal RNA (rRNA) gene copies in each fraction were quantified using a pan-bacterial broad-coverage quantitative PCR technique (Liu C M, Aziz M, Kachur S, Hsueh P-R, Huang Y-T, Keim P et al. (2012). BactQuant: an enhanced broad-coverage bacterial quantitative realtime PCR assay. *BMC Micronbrol* 12:56.). For fractions containing DNA (9-15 fractions per sample), bacterial 16S rRNA genes were amplified using 338F and 806R primers and sequenced using dual indexing (Fadrosh P, Ishizu A, Doucett R, Hart S C, Schwartz E, Menyailo O V et al. (2014). An improved dual-indexing approach for multiplexed 16S rRNA gene sequencing on the Illumina MiSeq platform. Microbiome 2: 6.) and 300-bp paired-end read chemistry on an Illumina MiSeq (Illumina, Inc., San Diego, Calif., USA). All sequences and accompanying metadata are available for download from MG-RAST (Meyer F, Paarmann D, D'Souza M, Olson R, Glass E M, Kubal M et al. (2008). The metagenomics RAST server—a public resource for the automatic phulogenetic and functional analysis of metagenome. *BMC Bioinform* 9:1.) project name hungate_qSIP, project ID 14151.

Data Analysis

Processing and quality filtering of sequences were performed as previously described in Examples 1 and 2. Reads were assigned to their originating samples using 24-bp dual-index barcodes formed by combining the 12-bp barcodes from each paired-end read. Primer sequences were trimmed, and then reads were stitched using FLASH (Fadrosh D W, Ma B, Gajer P, Sengamalay N, Ott S, Brotman R M et al. (2014). An improved dual-indexing approach for multiplexed 16S rRNA gene sequencing on the Illumina MiSeq platform. Microbiome 2: 6.). The full-length reads were clustered using the UCLUST-based open reference operational taxonomic unit (OTU) picking protocol described in QIIME (Caporaso J G, Kuczynski J, Stombaugh J, Bittinger K, Bushman F D, Costello E K et al. (2010). QIIME allows analysis of high throughput community sequencing data. Nat Methods 7: 335-336.) against the Greengenes 13_8 97% sequence identity reference database (McDonald D, Price M N, Goodrich J. Nawrocki E P, DeSantis T Z, Probst A et al. (2012). An improved Greengenes taxonomy with explicit ranks for ecological and evolutionary analyses of bacteria and archaea. ISME J 6: 610-618.). Taxa were analyzed at the 'species' level (L7 table in QIIME).

Figure 17A:
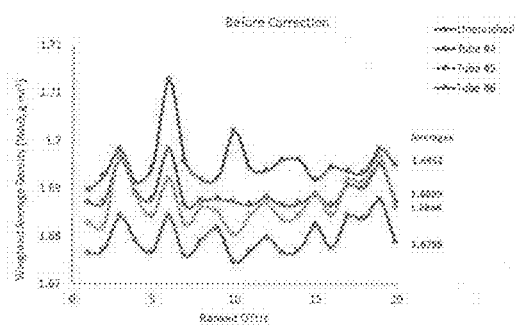
FIGS. 17A and 17B: Graphical representation of the approach used to quantify, and correct for, variation in weighted average density (WAD) estimates between ultra-centrifuge tubes. In this example weighted average density estimates for taxa in the bottom 5% of WAD shifts in the week one control treatment (in ranked order along the x-axis) are shown for each tube before and after the correction. The offset for each tube was calculated as offset$_{tubeX}$=Average WAD$_{tubeX}$-Average WAD$_{Unenriched}$, where the unenriched WAD is the average of WAD estimates from the corresponding no isotope control samples. The offset for each tube was then subtracted from the WAD estimate for all OTUs within that tube.
Figure 17B:
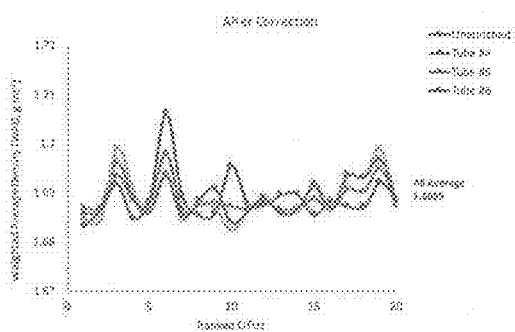

The excess atom fraction (EAF) $^{18}O$ and $^{13}C$ were calculated for each taxon as described previously in Examples 1 and 2. Briefly, a weighted average density was calculated for each taxon's DNA after incubation in the presence of unlabeled and isotopically enriched substrates (that is, water and glucose) based on its distribution across a CsCl density gradient. The shift in weighted average density following incubation with an isotopically enriched substrate can be used to quantify the amount of isotope incorporation based on the theoretically modeled and experimentally verified relationship between isotope incorporation and DNA molecular weight in Examples 1 and 2. Preliminary data analysis revealed an effect of ultracentrifuge tube on estimates of taxon-weighted average density. This effect is likely a consequence of slight differences in the CsCl density gradients between tubes. To correct this, we assumed that the taxa in the bottom 5% of weighted average density shifts in each treatment did not incorporate any isotope based on the evidence that a significant fraction of soil microorganisms are inactive (Lennon J T, Jones S E. (2011). Microbial seed banks: the ecological and evolutionary implications of dormancy. Nat Rev Microbiol 9: 119-130.; Blagodatskaya E, Kuzyakov Y. (2013). Active microorganisms in soil: critical review of estimation criteria and approaches. Soil Biol Biochem 67: 192-211.). The average difference between the unenriched weighted average density (average of no isotope tubes) and the observed weighted average density for these taxa was then used to quantify and correct for inter-tube variation in weighted average density estimates (as shown in FIGS. 17A and 17B).

Responses to labile C addition were assessed by comparing the increase in growth upon labile C addition ($\Delta^{18}O = ^{18}O_{glucose} - ^{18}O_{control}$) to the $^{13}C$ uptake. The relationship between these measures provides insight into the taxon-specific and community-level C usage. A decline in growth, indicated by a negative $\Delta^{18}O$ value, would indicate less soil organic matter consumption regardless of $^{13}C$ uptake. Additional growth using solely the added $^{13}C$-glucose would produce a ratio of $^{13}C$ to $\Delta^{18}O$ that is 42, because 100% of the C atoms in newly synthesized DNA would be derived from glucose, whereas only a fraction of the oxygen used for DNA synthesis comes from water, with the remainder coming from organic substrates. Escherichia coli grown in pure culture on glucose as the sole C source derives 33% of the oxygen in its DNA from water (Examples 1 and 2) and consequently would exhibit a $^{13}C/\Delta^{18}O \approx 3$. Based on the possibility that some organisms could derive a greater fraction of their oxygen from water, we estimated that growth solely on glucose could produce a $^{13}C/\Delta^{18}O$ as low as 2 meaning as much as 50% of the oxygen in DNA could be derived from water. This served to ensure our inference of additional soil C consumption (priming) based on a $^{13}C/\Delta^{18}O < 2$ was conservative. Integrated measures of whole community activity are presented as relative abundance weighted average $^{13}C$ and $\Delta^{18}O$ and the ratio between these values.

For phylogenetic analysis, a representative sequence for each taxon was aligned with the Greengenes 13_8 97% OTU reference database using BLAST as described in Morrissey and Franklin (2015). The reference sequence with the greatest identity match for each OTU was used for down-stream analyses; the median percent identity was 99%. The Greengenes 97% OTU tree was then pruned to contain only the OTUs present in our samples and visualized using the interactive tree of life. The responses of individual taxa were categorized as described based on their $^{13}C$ and $\Delta^{18}O$ as described below, and the net relatedness index was calculated for each group to see if the members were more or less phylogenetically related than would be expected by chance (Webb C O, Ackerly D D, McPeek M A, Donoghue M J. (2002). Phylogenies and community ecology. Annu Rev Ecol Syst 33: 475-505.) using the ses.mpd function in the picante R package (Kembel S W, Cowan P D, Helmus M R, Cornwell W K, Morlon H, Ackerly D D et al. (2011). Picante: R tools for integrating phylogenies and ecology. Bioinformatics 26: 1463-1464.). The relative abundance and isotope incorporation (EAF $^{13}C$ or $^{18}O$) of replicates were averaged before the regression and phylogenetic analysis.

All sequence data associated with this project have been deposited at MG-RAST (project accession number 14151, project name 'hungate_qSIP'), complete metadata are available on Figshare (doi.org/10.6084/m9.figshare.4600420.v1).

Results and Discussion

The amount of soil C primed gradually increased over the incubation period (FIG. 9), transitioning from slightly negative in week 1, after a single pulse of glucose, to positive in subsequent weeks. Such temporal dynamics are commonly observed in priming experiments and have been hypothesized to arise from microbial community dynamics. Here we show that priming is associated with changes in both the growth and C utilization of individual microbial taxa. Specifically, sustained availability of glucose through repeated pulses alters the utilization of native soil C in the majority of soil bacteria.

Figure 18:
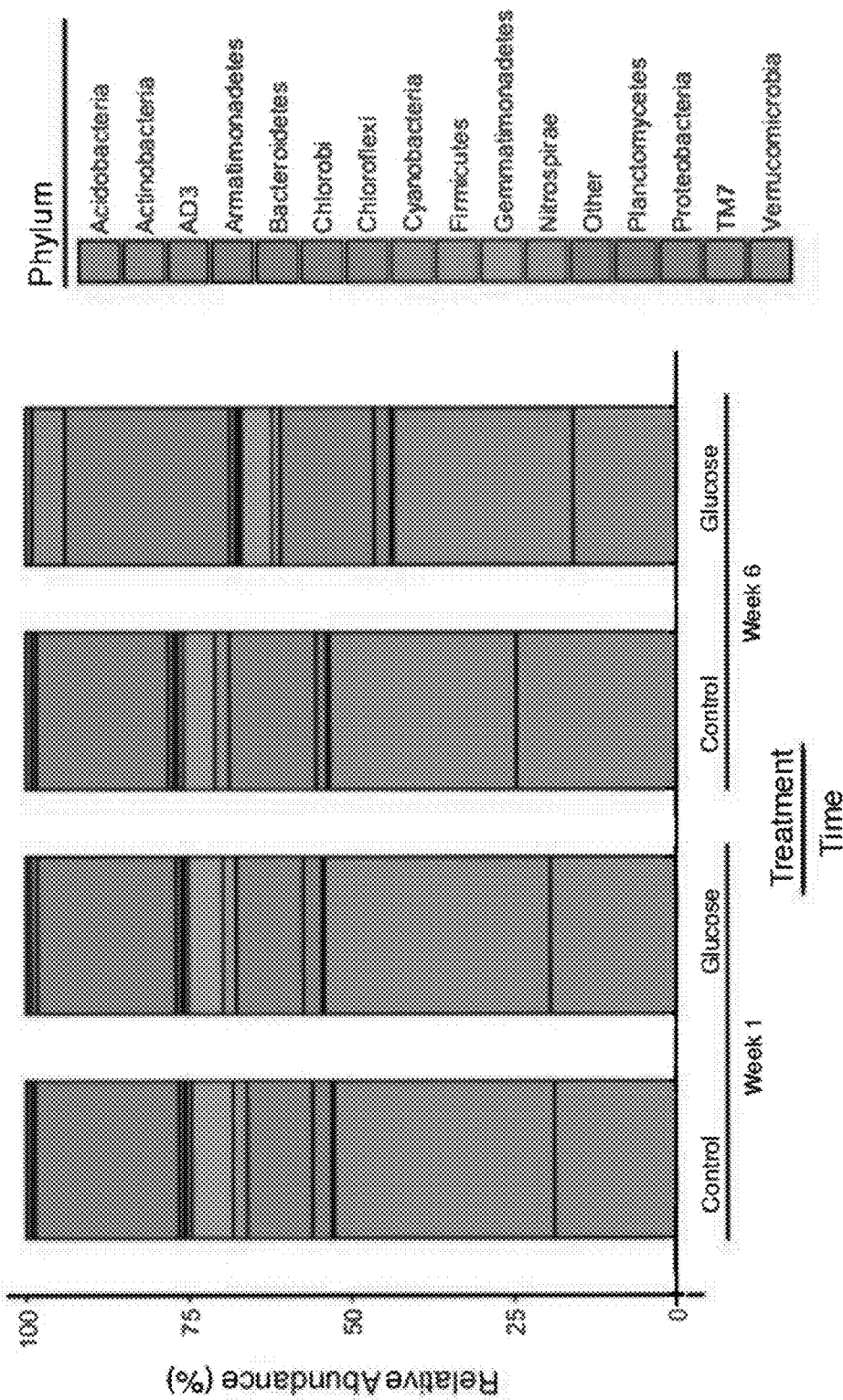
FIG. 18: Average relative abundance (% of 16S rRNA gene sequences) of dominant phyla (>1% of total sequences) in the control and glucose amended soils during weeks one and six.

Over the 6-week incubation, bacterial community composition shifted slightly in control soil and substantially in soil with added glucose (FIG. 10A; permutational multivariate analyses of variance week×treatment F=9.7, P<0.01). Repeated glucose additions increased the relative abundance of Proteobacteria (specifically α and δ) and TM7, whereas decreasing the proportion of Acidobacteria and Actinobacteria (FIG. 18).

In order to relate taxon-specific activity to priming, we examined the relationship between glucose use (via $^{13}C$ assimilation) and the change in growth ($^{18}O$ assimilation) because of glucose addition ($\Delta^{18}O$) for all taxa, weighted by their relative abundances (FIG. 10B). Increased growth using $^{13}C$-glucose as the sole C source would produce a $^{13}C/\Delta^{18}O$ ratio of at least 2. This is because 100% of the C atoms in newly synthesized DNA would be derived from glucose, whereas only a fraction (~50% maximum) of the oxygen used for DNA synthesis comes from water (see Materials and methods, Hungate et al., 2015). Increased growth with lower than expected $^{13}C$ assimilation from the added glucose ($^{13}C/\Delta^{18}O < 2$) is possible by enhanced consumption of SOC. Consequently, the relationship between $\Delta^{18}O$ and $^{13}C$ assimilation in weeks 1 and 6 (FIG. 10B) can be used to understand individual and community-level responses to glucose addition and reveal how the aggregated activity of individual taxa mediates the priming of SOC.

After single and repeated pulses of glucose, changes in growth were strongly and positively correlated with glucose assimilation (FIG. 10B, both P<0.001) suggesting a direct stimulation of activity within individual taxa. Similarly, our results suggest that the large majority of microorganisms consumed the added glucose, after single and repeated pulses, as their $^{13}$C atom percent excess was above zero (FIG. 10B). This is consistent with a recent study using RNA-stable isotope probing, which found no differences in fresh organic matter utilization across taxonomic groups (Thomson et al., 2014).

Figure 9:
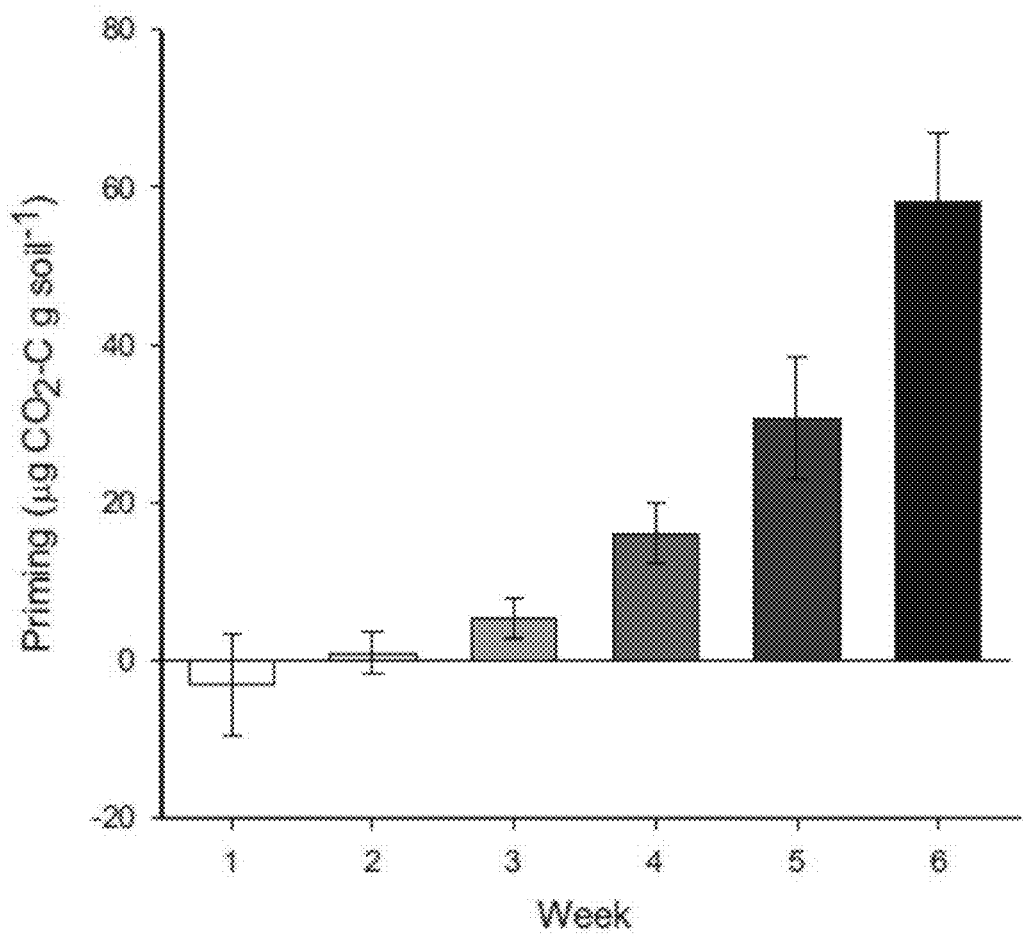
FIG. 9: weekly soil organic matter priming (mean±s.e.), calculated as the difference in soil derived C mineralized in glucose-added and unamended soil. Mineralization rates were evaluated in laboratory microcosms of soil from a ponderosa pine forest receiving weekly additions of glucose or water.

Following a single pulse of glucose, many bacterial taxa (42% of taxa accounting for 39%/0 of 16S rRNA gene sequences) consumed the added glucose with-out exhibiting increased growth rates (average $^{13}$C=0.078 EAF for organisms with $\Delta^{18}$O<0). This suggests that glucose was being consumed in lieu of SOC, a phenomenon often called preferential substrate utilization. Preferential substrate utilization provides a mechanism by which the introduction of labile C can decrease SOC utilization (negative priming). When considering the community as a whole, the substantial assimilation of labile C (average $^{13}$C=0.101 EAF) was accompanied by only a marginal increase in growth rate (average $\Delta^{18}$O=0.016 EAF). This produced a community average $^{13}$C/$\Delta^{18}$O of 6.31, much higher than is expected for normal soil organic matter consumption and additional growth using glucose as the sole C source. These data suggest the majority of taxa used the added glucose in lieu of their normal SOC consumption, and very few bacteria increased their use of SOC in response to a single pulse of substrate addition. Consequently, the use of SOC was decreased relative to the control soil, resulting in negative priming, a finding in line with the slightly negative change in SOC mineralization observed during week 1 (FIG. 9).

By week 6, after repeated glucose addition, the bacterial community response was consistent with enhanced SOC utilization (positive priming). At this time, fewer organisms consumed glucose without a corresponding increase in growth (22% of taxa accounting for 7% of 16S rRNA gene sequences), and glucose consumption by these organisms was much lower than in week 1 (average $^{13}$C=0.032 EAF for organisms with $\Delta^{18}$O<0), indicating a reduction in preferential substrate utilization. When examining the community as a whole, the glucose uptake (average $^{13}$C=0.061 EAF) could not account for the increase in growth (average $\Delta^{18}$O=0.039 EAF), indicating that bacteria must have increased their consumption of SOC (average $^{13}$C/$\Delta^{18}$O=1.56). Sustained glucose addition enhanced bacterial growth and SOC utilization, thereby priming the decomposition of SOC in week 6 (FIG. 9).

To better understand how individual taxa and phylogenetic groups gave rise to these community-level dynamics, we placed each taxon into one of three categories based on the change in growth rate in response to glucose addition ($\Delta^{18}$O) and the reliance on glucose as a C source for this extra growth ($^{13}$C): (1) reduced: taxa that exhibited a reduction in growth rate ($\Delta^{18}$O<0), (2) enhanced—glucose C: taxa whose growth rates were enhanced with sufficient $^{13}$C consumption, such that there is no evidence of additional soil organic matter usage ($\Delta^{18}$O≥0 and $^{13}$C/$\Delta^{18}$O≥2) and (3) enhanced mixed C: taxa with enhanced growth rates that was at least partly because of use of SOC as a C source ($\Delta^{18}$O≥0 and $^{13}$C/$\Delta^{18}$O<2). Reduced growth is associated with reduced SOC consumption (negative priming). Enhanced growth via the consumption of a mixture of the added labile C and SOC (enhanced—mixed C) indicates positive priming. For organisms that consumed glucose in excess of that necessary to explain their increase in growth (enhanced—glucose C), there are two possibilities: they could have caused no priming, if their glucose consumption was in addition to their normal SOC consumption; or they could have caused negative priming, if their glucose consumption substituted for some of their normal SOC consumption.

Figure 11:
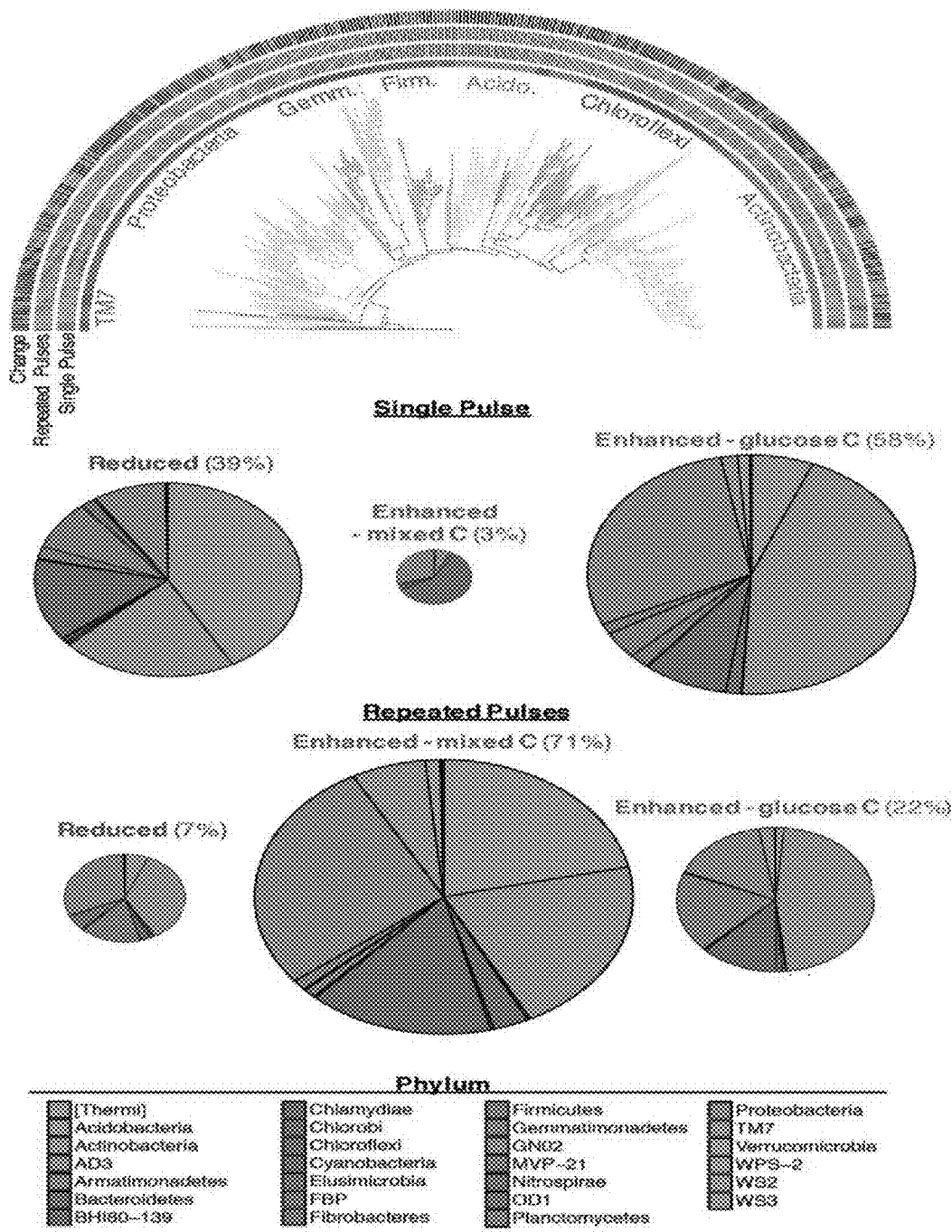
FIG. 11: Phylogeny of bacterial taxa and each taxon's growth response to single and repeated pulses of glucose. Phyla are indicated by color and dominant groups are annotated. Growth responses during weeks 1 and 6, as well as the change in response between these weeks, are designated using color strips. Pie charts display the proportion (%) and phylum-level composition of 16S rRNA gene sequences in each response category.

Few organisms enhanced their consumption of SOC (enhanced mixed C) in response to a single pulse of glucose. Instead, most either reduced their growth or exhibited enhanced growth using the added glucose (FIGS. 10 and 11). However, after repeated glucose additions, the number of microbial taxa with enhanced growth based on a mix of glucose and SOC (enhanced—mixed C) increased substantially: 64% of bacterial taxa changed categories in response to multiple C pulses, with the majority of those (163 of 237, 69%) transitioning from reduced or enhanced—labile C to enhanced—mixed C (FIG. 11), in other words, transitioning to an isotopic signature indicative of priming.

Taxa involved in the positive priming of SOC (that is, enhanced—mixed C) were not phylogenetically clustered at any time (Table 2, FIG. 11). Similarly, the widespread transition in response to repeated glucose addition was not phylogenetically constrained. This suggests that enhanced SOC utilization in response to sustained labile C addition (priming) is a prototypical bacterial activity in soil that does not require any specialized ecophysiological characteristics, but instead results from fundamental requirements for balanced microbial growth. It is perhaps not surprising that a diverse majority of microorganisms use both C sources given that glucose is considered a relatively universal substrate and soil organic matter consists of a variety of compounds. Our findings support a scenario where the initial pulse of glucose addition alleviates C limitation and is used directly for growth. During this period, other nutrients are likely to be quickly immobilized, which, in turn, triggers the production of extracellular enzymes. These enzymes then gradually facilitate the priming of native soil C by liberating monomeric C as microbes 'mine' for other macro- and micronutrients, producing the positive priming response we observed after multiple pulses of glucose. Thus, our results substantiate microbe-based models developed to explain soil C cycling dynamics and are congruent with the nitrogen mining hypothesis.

TABLE 2

Phylogenetic clustering, assessed using the NRI, in the growth responses of bacteria to single and repeated pulses of glucose, as well as the consistency in response

|  | NRI | P-value |
|---|---|---|
| Single pulse | | |
| Reduced | 0.00 | 0.52 |
| Enhanced - mixed C | −1.21 | 0.80 |
| Enhanced - glucose C | 2.04 | 0.04* |
| Repeated pulses | | |
| Reduced | 2.88 | 0.03* |
| Enhanced - mixed C | −2.03 | 0.00 |
| Enhanced - glucose C | 2.21 | 0.01* |
| Change | | |
| Altered response | −2.43 | 0.99 |

TABLE 2-continued

Phylogenetic clustering, assessed using the NRI, in the growth responses of bacteria to single and repeated pulses of glucose, as well as the consistency in response

|  | NRI | P-value |
|---|---|---|
| Consistent response |  |  |
| Reduced | 1.95 | 0.03* |
| Enhanced - mixed C | 0.17 | 0.58 |
| Enhanced - glucose C | 3.98 | <0.01* |

Abbreviations:
C, carbon,
NRI, net relatedness index
*Significant, n = 0.05

However, these results stand in opposition to our hypothesis that microorganisms exhibit consistent and phylogenetically clustered patterns of C use reflective of their ecological strategy. Instead we found that many organisms switched from using glucose C to using a mixture of glucose and SOC for additional growth, indicating plasticity in their C use. Bacteria are known to regulate their growth and substrate use in culture, but this has been difficult to observe directly in situ. However, nucleic acid labeling techniques have shown that many microbial taxa can use a variety of C substrates in their natural assemblages. The metabolic flexibility observed in this study—where many microbial taxa can effectively compete for labile C while also having the capacity to utilize presumably more recalcitrant soil organic matter—provides insight into the ecology of these organisms. Specifically, it suggests that the majority of organisms in our soil cannot be neatly defined as copiotrophs specializing on labile C or as oligotrophs specializing on the more recalcitrant organic matter. Instead these organisms are metabolically flexible enough to adjust their C use to suit the changing resource environment. Consequently, our results highlight the need to characterize the physiological flexibility of microorganisms in their natural environments in order to understand the functional relevance of microbial community composition.

As suggested above, our results contradict the hypothesis that one group of organisms consume the labile C (copiotrophic or r-strategist), and this activity indirectly stimulates a taxonomically distinct group of microorganisms (oligotrophic or K-strategist), that consume additional SOC. Rather, we found that most taxa whose growth was increased by glucose addition ended up consuming a mix of glucose and SOC (FIGS. 10B and 11), suggesting a direct stimulation of activity within individual taxa.

Although priming exhibited no phylogenetic clustering among the taxa involved, other responses to glucose addition were phylogenetically clustered (Table 2, FIG. 11). After a single pulse of glucose, only the enhanced—glucose C group was clustered, with the majority of taxa in several broad taxonomic assemblages, including Actinobacteria (65% of member taxa), Verrucomicrobia (78%) and β-Proteobacteria (79%) exhibiting this response. Similarly, after repeated pulses of glucose, both the reduced and enhanced—glucose C groups were phylogenetically clustered. Many of the taxa that were reduced or enhanced using the glucose after multiple pulses also exhibited those responses initially (after a single pulse), suggesting a consistent response to glucose over the course of the experiment (FIG. 11). A persistent reduction in growth upon glucose addition was seen in most Formicates (52%) and in all members of Nitrospirae. Enhanced growth using glucose was consistently observed within multiple Actinobacteria families, including Micro-monosporaceae (57%), Nocardioidaceae (67%) and Streptomycetaceae (75%).

Phylogenetic clustering of organisms in the reduced and enhanced—glucose C groups suggests that these responses to labile C addition are brought about by physiological or ecological traits that are evolutionarily conserved. Reduced growth after labile C addition could reflect an oligotrophic ecological strategy, as low-resource-adapted organisms are expected to be outcompeted by copiotrophs in nutrient-rich environments. This could underlie the reduced growth of Firmicutes observed in this experiment; these taxa were primarily within the class Bacilli, a diverse group containing both relatively copiotrophic and oligotrophic 'species'. Within Bacilli, these growth strategies have been found to sort by phylogeny in cultured representatives. This phylogenetic clustering in growth response could arise from conserved physiological attributes, and indeed characteristics consistent with adaptation to a low-resource environment have been described in *Bacilli* spp., including small genome size, and the ability to maintain near-zero-specific growth rates. In the case of Nitrospirae, reduced growth may have resulted from glucose-induced reductions in nitrogen availability, which take place rapidly after labile C addition to soil, creating a nitrogen-scarce environment. Nitrospirae may be particularly sensitive to reductions in N availability as these organisms use nitrogen for both energy and biomass production.

The taxa that consistently enhanced their growth using only the added glucose (enhanced—glucose C) were also phylogenetically clustered (Table 2). These included Actinobacteria within the order Actinomycetales, previously shown to exhibit enhanced growth with labile C, and favor rhizosphere environments. Phylogenetic clustering of organisms that prefer labile C could reflect a conserved genomic basis for opportunism within soil bacteria or sensitive catabolite repression of alternate C degrading metabolic pathways.

Although we found agreement between the activity of bacterial taxa and the priming of soil C, this picture is likely incomplete as other soil heterotrophs, most notably fungi, were not examined. Similarly, because the current work only considered a single ecosystem and utilized experimental microcosms, additional research is necessary to determine whether our findings can be widely generalized to natural systems. However, using this technique, we were able to quantify taxon-specific activities in situ, and gain a clearer picture of how individual bacterial 'species' respond to C addition. In the soil, we assessed, positive priming was caused by the majority of soil bacteria, organisms that were not phylogenetically constrained, suggesting that the priming effect may not depend upon specialized phylogenetic groups. Our findings also suggest that many bacterial taxa can exhibit plasticity with regard to C use, changes in C use that could underlie the emergence of positive priming following the addition of labile C. Examining these dynamics in a broad range of soils could test whether this ubiquity of priming across bacteria biodiversity contributes to the widespread occurrence of positive priming in soil.

Example 4—Identification of Growing Bacteria During Litter Decomposition in Freshwater Through $H_2^{18}O$ Quantitative Stable Isotope Probing Experimental Procedures
Incubations Senescent leaves from 10 *Populus fremontii* trees were collected using bridal veil netting at Beaver Creek, Ariz., and air-dried in the fall of 2013. Stream water and sediment were also collected from Beaver Creek in January of 2015. Freshwater microcosm were set up in 15 mL Falcon tubes in triplicate as follows: 2 g of sediment, 9 mL of stream water and 50 *Populus fremontii* leaf discs (0.13 g-0.15 g) were incubated at room temperature in a shaker at 160 r.p.m. for 10 days to allow bacteria to colonize the leaves. The lids of the Falcon tubes were left slightly unscrewed to allow air exchange. After 10 days the Falcon tubes were centrifuged at 2250×g for 10 min, and the supernatant was removed. The stream water was then replaced by 1 mL of $H_2^{18}O$ (treatment) or sterile nanopure water (control), and the microcosms were incubated for an additional 8 days. DNA was extracted from leaf discs using a MoBio Powersoil Powerlyzer DNA extraction kit following the manufacturer's instructions with the addition of an initial 5 min incubation at 72° C. after the bead solution was added.

Centrifugation and Fractionation

To separate DNA by density, 1000 ng of DNA was added to 2.51 mL of cesium chloride (1.9 g mL$^{-1}$), 0.49 mL of gradient buffer (200 mM trisaminomethane (Tris), pH 8, 200 mM potassium chloride, 2 mM Ethylenediaminetetraacetic acid (EDTA) in an OptiSeal® ultracentrifuge tube (Beckman Coulter, Brea, Calif.). The tubes were spun at 127,000×g at 18° C. for 72 h using a Beckman TLN-100 rotor in an Optima™ MAX ultracentrifuge (Beckman Coulter, Brea, Calif.). Approximately 3 mL of the cesium chloride gradient was separated into fifteen 200 µL fractions. The density of each fraction was measured using a Reichert AR 200 handheld digital refractometer (Reichert Technologies, Buffalo, N.Y.). The DNA present in each fraction was precipitated with isopropanol, cleaned with ethanol and resuspended in 50 µL of Tris-EDTA buffer. The DNA concentrations were determined with the Qubit (Invitrogen, Carlsbad, Calif.) HS dsDNA assay. A density curve with the proportion of total DNA as a function of density in the $H_2^{16}O$ and $H_2^{18}O$ treatments was graphed to determine if the $^{18}O$ isotope was incorporated into DNA. We used a Student's t-test to compare the weighted average densities of the $^{16}O$ and $^{18}O$ treatments.

qPCR

Quantitative PCR was used to measure bacterial 16S rRNA gene abundance. Standard curves were generated using 10-fold serial dilutions of 16S rRNA gene amplicons which were prepared using soil DNA and primers 515F(5'-GTGCCAGCMGCCGCGGTAA-3' (SEQ ID: NO. 6)) and 806R (5'-GGACTACVSGGGTATCTAAT-3'(SEQ ID: NO. 7)) (Caporaso, J. G., Lauber, C. L., Walters, W. A., Berg-Lyons, D. Huntley. J., Fierer, N., et al. (2012) Ultra-high-through-put microbial community analysis on the Illumina HiSeq and MiSeq platforms. ISME 6: 1621-1624.) containing Illumina sequence adaptors P5 (5'-AATGATACGGC-GACCACCGA (SEQ ID: NO. 8)) and P7 (5'-CAAGCA-GAAGACGGCATACGA (SEQ ID: NO. 9)) at the 5' end of each primer, respectively, to prevent decreased primer efficiency due to amplicon degradation (Dhanasekaran, S., Doherty, T. M., and Kenneth, J; TB Trials Study Group. (2010) Comparison of different standards for real-time PCR-based absolute quantification. J Immunol Methods 354: 34-39.). The 8 µL qPCR reactions contained 0.2 mM of each primer, 0.01 U µL$^{-1}$ Phusion HotStart II Polymerase (Thermo Fisher Scientific, Waltham Mass.), 1× Phusion HF buffer (Thermo Fisher Scientific), 3.0 mM MgCl$_2$, 6% glycerol and 200 µM dNTPs. The assay was performed on an Eppendorf Master-cycler ep Realplex system (Eppendorf. Westbury N.Y.), using a program of 95° C. for 1 min followed by 44 cycles of 95° C. for 30 s, 64.5° C. for 30 s and 72° C. for 1 min. Gel electrophoresis was performed to confirm the size of the amplified products. Bacterial gene copy numbers were calculated using a regression equation for each assay relating the cycle threshold (Ct) value to the known number of copies in the standards. All qPCR reactions were run in triplicate.

Sequencing

Two PCR steps were used to process the samples (Berry et al., 2011). Each sample was first amplified using primers 515F and 806R This was done in triplicate 8 µL PCR reactions containing 1 mM of each primer, 0.01 U µL$^{-1}$ Phusion HotStart II Polymerase (Thermo Fisher Scientific, Waltham Mass.), 1× Phusion HF buffer (Thermo Fisher Scientific), 3.0 mM MgCl$_2$, 6% glycerol and 200 µM dNTPs. PCR conditions were 95° C. for 2 min; 15 cycles of 95° C. for 30 s, 55° C. for 30 s and 60° C. for 4 min. Initial PCR reaction products were checked on a 1% agarose gel, pooled, 10-fold diluted, and used as template in the subsequent tailing reaction with region-specific primers that included the Illumina flowcell adapter sequences and a 12 nucleotide Golay barcode (15 cycles identical to initial amplification conditions). Products of the tailing reaction were purified with carboxylated SeraMag Speed Beads (Sigma-Aldrich, St. Louis, Mo.) at a 1:1 v/v ratio as described in Rohland, N., and Reich, D. (2012) Cost-effective, high-throughput DNA sequencing libraries for multiplexed target capture. Genome Res 22: 939-946 and quantified by Picogreen fluorescence. Equal quantities of the reaction products were then pooled; the library was bead-purified once again (1:1 ratio), quantified by qPCR using the Library Quantification Kit for Illumina (Kapa Biosciences, Woburn, Mass.), and loaded at 11 pM (including a 30% PhiX control) onto an Illumina MiSeq instrument (San Diego, Calif.) using 2×150 paired-end read chemistry. The flowcell produced 973±114 K clusters per mm$^2$, returning over 14 million clusters passing filter.

Data Analysis

The DNA sequences were analysed with the software package Quantitative Insights into Microbial Ecology v1.7 (QIIME) (Caporaso, J. G., Kuczynski, J., Stombaugh, J., Bittinger, K., Bushman, F. D., Costello, E. K., et al. (2010a) QIIME allows analysis of high-throughput community sequencing data. Nat Methods 7: 335-336). For quality filtering, the default score was changed from 25 to 30. Open reference OTU picking was performed at 97% identity using uclust (Edgar, R. C. (2010) Search and clustering orders of magnitude faster than BLAST. Bioinformatics 26: 2460-2461). The most abundant sequence for each OTU was aligned with PyNAST (Caporaso, J. G., Bittinger, K., Bushman, F. D., DeSantis, T. Z., Andersen, G. L., and Knight, R. (2010b) PyNAST: a flexible tool for aligning sequences to a template alignment. Bioinformatics 26: 266-267) against the Greengenes v13_5 database (DeSantis, T. Z., Hugenholtz, P., Larsen, N., Rojas, M., Brodie, E. L., Keller, K., et al. (2006) Greengenes, a chimera-checked 16S rRNA gene database and work-bench compatible with ARB. Appl Environ Microbiol 72: 5069-5072). Taxonomy was assigned using Ribosomal Data Project classifier (Wang, Q., Garrity, G. M., Tiedje, J. M., and Cole. J. R. (2007) Naive Bayesian classifier for rapid assignment of rRNA sequences into the new bacterial taxonomy. Appl Environ Microbiol 73: 5261-5267) and a phylogenetic tree was built. Any OTUs that accounted for less than 0.05% of the total sequences were discarded (Bokulich, N. A., Subramanian, S., Faith, J. J., Gevers, D., Gordon, J. I., Knight, R., et al. (2013) Quality-filtering vastly improves diversity estimates from Illumina amplicon sequencing. Nat Methods 10: 57-59). The bacterial libraries were rarefied so that sequencing efforts did not affect diversity comparisons. The QIIME L7 species level OTU table was used for subsequent analyses. The L7 table groups together OTUs that are phylogenetically similar without accounting for intraspecific genetic diversity in the V4 region. OTUs that have been assigned the same species may represent different strains, but may also be sequencing errors that artificially inflate diversity. All sequences have been deposited at MG-RAST, project ID 239736.

Isotopic composition of individual taxa after exposure to $H_2{}^{18}O$ was calculated as described by Examples 1 and 2. Briefly, for each fraction the total number of 16S rRNA gene copies was measured using qPCR, and the proportion of 16S rRNA gene copies for each bacterial taxon within that fraction was determined by multiplying the total number of 16S rRNA gene copies by the relative abundances obtained from sequencing. The density for each bacterial taxon was computed as a weighted average, summing the densities across all fractions times the total number of 16S rRNA gene copies in that fraction expressed as a proportion of the total 16S rRNA gene copies. The increase in weighted density relative to the weighted density of the unlabeled treatments was calculated. We determined the GC content of the DNA for each taxon, based on its density, using the relationship of GC content and density based on a pure culture study by Examples 1 and 2. The GC content was then used to calculate the molecular weights and the corresponding values of $^{18}O$ isotope composition for each taxon (see Supporting Information for calculations). Bootstrap resampling (with replacement, 1000 iterations) of replicates within each treatment was used to estimate taxon-specific 90% confidence intervals for the change in density and the corresponding value of $^{18}O$ atom fraction excess isotope composition. We measured the abundances of a taxon at the class level as a fraction of the total sequences characterized times the number of bacterial 16S rRNA gene copies. All calculations were performed in R (R Development Core Team, 2011).

Results and Discussion

SIP in aquatic environments with $H_2{}^{18}O$ was not previously explored because it may be difficult to achieve sufficient levels of nucleic acid labeling in samples containing large amounts of non-enriched water. To overcome this problem, we replaced the non-enriched environmental water with 97 atom % $H_2{}^{18}O$; an experimental approach that may also be applicable to saturated soil or sediment samples. This allowed the DNA of the bacterial community growing on decomposing litter in an aqueous sample to become sufficiently enriched with $^{18}O$ derived from $H_2{}^{18}O$ to separate it from the non-labeled DNA (t=24.29, p=0.01) (FIG. 12A).

We used bootstrapping to determine a 90% CI for the atom fraction excess isotope composition of each bacterial taxon (Examples 1 and 2). Sequencing of 16S rRNA gene amplicons generated 6.4 million reads that clustered into 834 operational taxonomic units (OTUs) and grouped into 236 single species at the 97% sequence similarity level. Taxa were considered to be growing and included into our analysis if the confidence interval for atom fraction excess did not overlap zero. Using this criterion, out of 236 taxa, 128 grew and incorporated sufficient $^{18}O$ isotopic tracer into their DNA (FIG. 13A). Proteobacteria accounted for more than 45% of the 16S rRNA genes in the growing community, followed by Bacteroidetes (30%) and Firmicutes (10%). Other studies have shown that Proteobacteria were the most abundant phylum of freshwater bacteria associated with leaf litter, and in planktonic and biofilm communities in streams, where they break down recalcitrant carbon compounds found in leaf litter, or utilize degradation products and plant leachate like acetate and phenol.

Figure 13B:
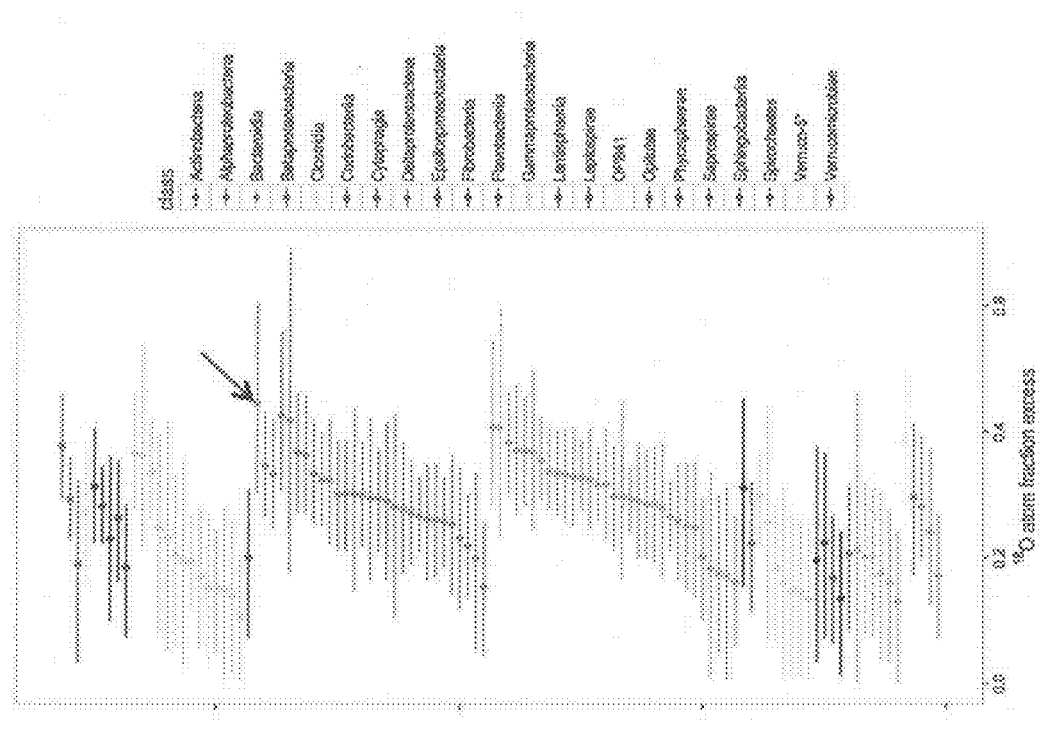
FIGS. 13A and B: Median isotopic enrichment of individual taxa with 90% confidence intervals. This shows the taxa colored by phylum. Taxa with confidence intervals that did not overlap zero incorporated significant amounts of $^{18}O$ and were considered growing. Taxa with confidence intervals that did overlap zero were excluded from further analysis. This shows the growing taxa only, coloured by class. The organisms with the highest atom fraction excess, *Desulfovibrio mexicanus*, is indicated by an arrow. The asterisk represents subdivision 5 of the Verrucomicrobia.
Figure 13A:
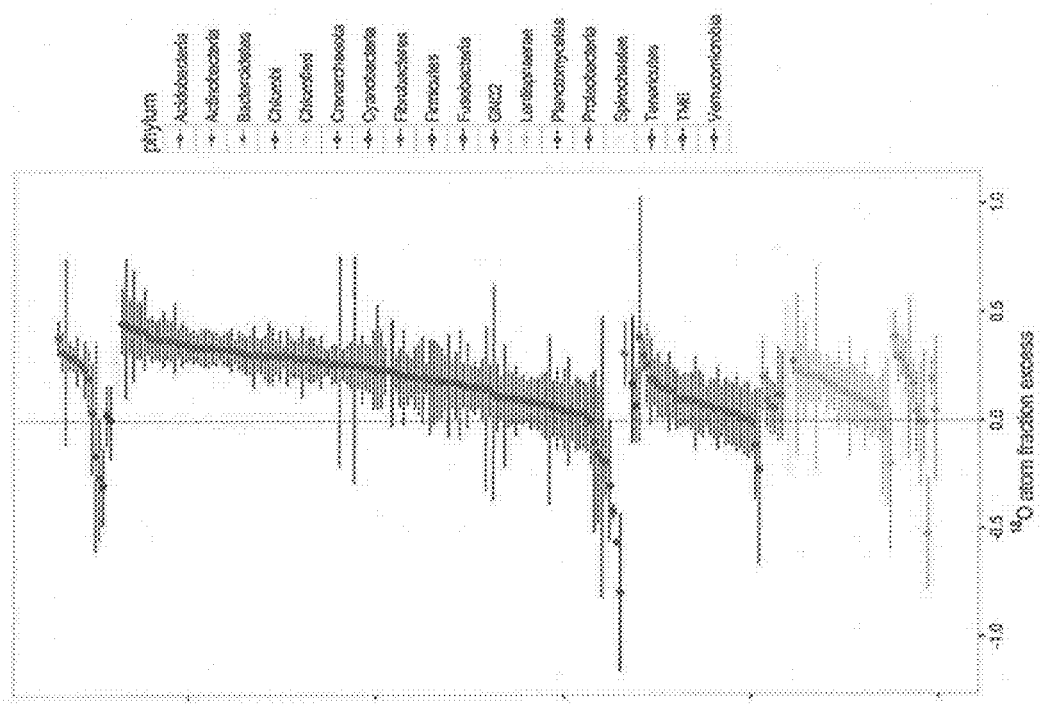

Quantitative SIP allowed identification of individual taxa with large $^{18}O$ enrichment, a proxy for growth (FIGS. 13A and 13B). Of the growing organisms, the greatest enrichment at the class level were observed for the unidentified Actinomycete OPB41 and d-Proteobacteria (excess $^{18}O$ enrichment of 0.384 and 0.375 respectively). Flavobacteriia, Saprospirae and Bacteroidia had the lowest excess $^{18}O$ enrichment with 0.135, 0.169 and 0.180 respectively (FIG. 13B). At the species level, *Desulfovibrio mexicanus*, a sulfate-reducing bacterium in the phylum d-Proteobacteria (Hernandez-Eugenio et al., 2000) had a large increase in weighted average density (FIG. 12A) and the highest atom fraction excess (0.445, FIG. 13B). Culture studies using *Escherichia coli* showed that 33% of the oxygen incorporated into newly synthesized DNA was derived from water (Examples 1 and 2). The increased isotopic labeling we observed in this study may be possible in organisms that obtain most of their O atoms from water and not from food, for instance organisms that feed on lipids, organic pollutants or labeled substrate.

DNA is primarily synthesized during cell division; therefore the DNA of a newly divided cell will be highly enriched in $^{18}O$ relative to a dormant or non-dividing cell. It is possible that some populations rely on recycling or scavenging deoxyribonucleotides while others make them de novo, thereby skewing a direct relationship between $^{18}O$ enrichment and new cells formed. However, we do expect that organisms that synthesize deoxyribonucleotides incorporate more $^{18}O$ per base pair DNA than nucleotide recycling/scavenging taxa. To relate enrichment levels directly to changes in cell densities also requires assumptions about the DNA extraction efficiency and the number of 16S rRNA genes in a bacterial genome.

Figure 14:
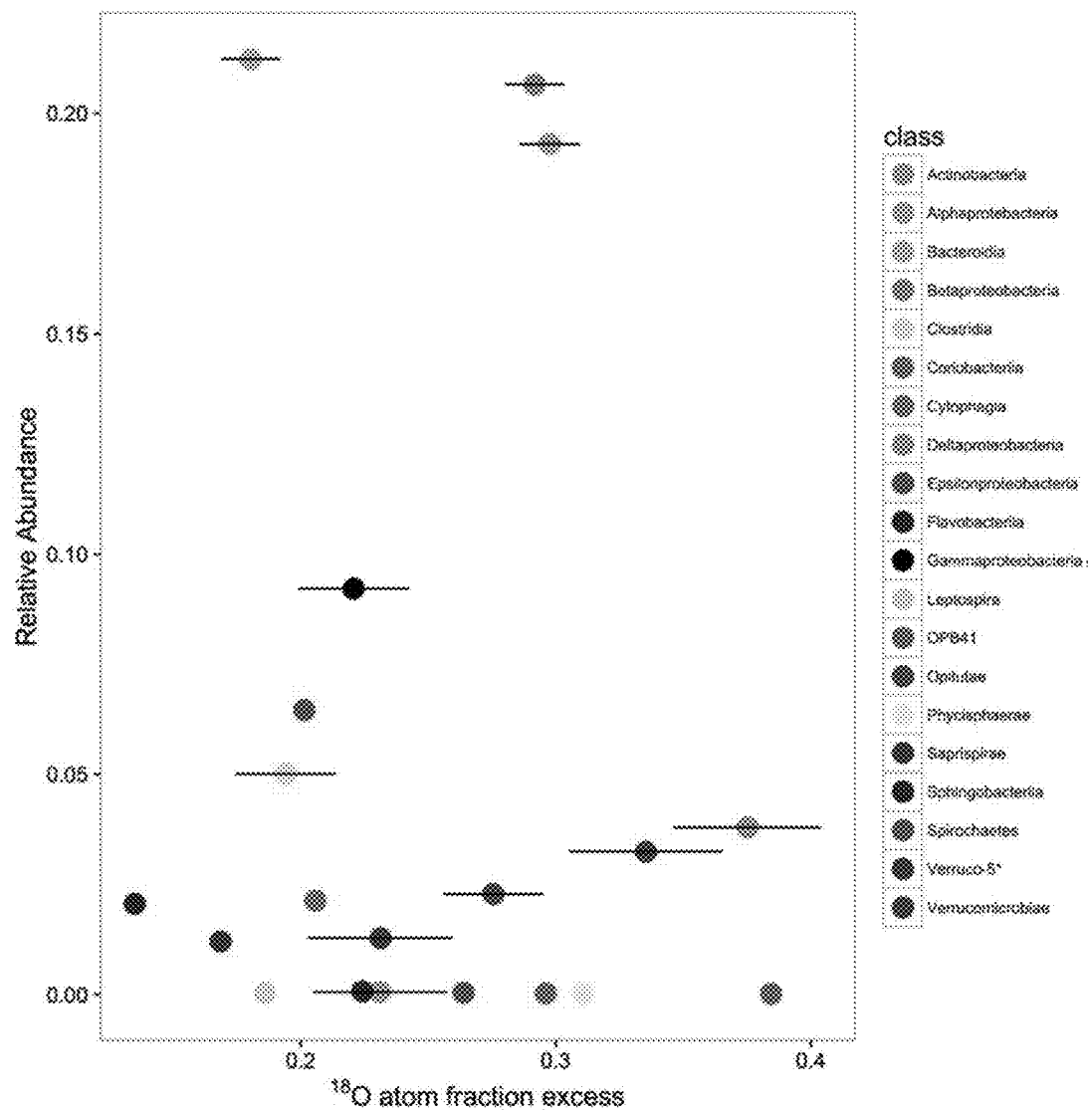
FIG. 14: Relationship between relative abundance and $^{18}O$ isotopic enrichment of DNA, an indicator of growth rate. Error bars represent standard errors. The asterisk represents subdivision 5 of the Verrucomicrobia.

We did not observe a linear relationship between the enrichment of a taxon and the abundance of that taxon, measured as the product of the fraction of the total sequences characterized and the number of bacterial 16S rRNA gene copies (FIG. 14). The DNA of the most abundant taxon at the class level, the Bacteroidia (21%), was not highly enriched, while other abundant taxa, such as the α- and β-Proteobacteria, had marginally above average $^{18}O$ enrichment values. Other taxa, for example Cytophagia and γ-Proteobacteria, were less enriched (0.206 and 0.221 excess $^{18}O$ enrichment) and less abundant (2.1% and 9% respectively). The δ-Proteobacteria were not very abundant at 3.8% of the community, and the unidentified Actinomycetes OPB41 were quite rare (0.018%), yet both taxa were highly enriched. Jones and Lennon (2010) found an inverse relationship between taxon abundance and taxon activity in lake microbial communities, and low abundant members of the 'rare biosphere' have been described as ecologically significant, possibly providing a seed bank (Jones, S. E., and Lennon, J. T. (2010) Dormancy contributes to the maintenance of microbial diversity. Proc Natl Acad Sci USA 107: 5881-5886.) that can influence microbial diversity and community composition in response to seasonal, or environmental changes.

Field observations of stream bacteria on leaves show that species richness increases through time, and our study provides a snapshot of these bacterial population dynamics during litter decomposition. Abundant taxa with low $^{18}O$ incorporation into their genomes could have been active during early stages of leaf litter decomposition, when the labeled water had not been added yet. Copiotrophic organisms like the Bacteroidetes, for instance, may be able to colonize freshly added *Populus fremontii* leaves early and grow quickly. The Actinobacteria, major contributors to the decomposition of litter in freshwater environments, only comprised a very small portion of the community in our study, possibly because they are involved during later stages of decomposition. We sampled one point in time to demonstrate the feasibility and utility of this technique. Multiple sampling dates could reveal if there is a shift through time in the growing bacterial assemblage.

This study demonstrates isotopic labeling of freshwater bacteria with $^{18}O$ from $^{18}O$-water through a quantitative approach that quantifies nucleic acid enrichment of individual taxa. There are multiple applications for this technique, including: (1) using qSIP to compare activity levels of other microbial species, such as fungi, during leaf litter decomposition. (2) combining qSIP with field surveys to characterize microbial growth rates under different environmental conditions, (3) combining qSIP with manipulative experiments to determine how microbial growth of different taxonomic groups is affected (e.g., Morrissey, E. M., Mau, R. L., Schwartz, E., Caporaso, J. G., Dijkstra, P., van Gestel, N., et al. (2016) Phylogenetic organization of bacterial activity. ISME J 1: 5).

Example 5—Stable Isotope Probing with $^{18}O$-Water to Investigate Bacterial Growth and Death in Environmental Samples Labeling Microbial DNA with $^{18}O$-Water SIP experiments require microorganisms to be exposed to enough $^{18}O$-water to label nucleic acids sufficiently for separation from nonlabeled nucleic acids by density along a cesium chloride gradient. The degree of separation is a function of the isotopic composition of the added water and of the duration of exposure. For *Escherichia coli* cells grown in culture, 23.75 atom % $^{18}O$-water for 24 hours was required to separate labeled from non-labeled DNA, but superior separation was achieved with even higher atom % values of $^{18}O$ (Schwartz E: Characterization of growing microorganisms in soil by stable isotope probing with $H_2^{18}O$. Appl Environ Microbiol 2007, 73: 2541-2546). Given the complexity and increased variability of intact microbial communities, initial SIP experiments in soils focused on rewetting of dry soils with 97 atom % $^{18}O$-water. Native soil water can be replaced by drying a soil sample and rewetting with $^{18}O$-water, arguably simulating a drying-rewetting cycle. Simply allowing soil to air dry at room temperature and adding 200 mL/g soil of $^{18}O$-water results in sufficiently labeled soil water to enable SIP. Conceivably, SIP with $^{18}O$-water could also be applied to wet soils—or even sediments—by replacing a large fraction of the native water with 97 atom % $^{18}O$-water. For example, by flushing a soil sample multiple times with $^{18}O$-water, one could increase the $^{18}O$ content of soil water without causing a drying-rewetting cycle. With these approaches, SIP with $^{18}O$-water could be applied to a wide variety of hydrologic conditions that occur in soils. It is also possible to incubate decaying organic matter in $^{18}O$-water, simulating organic matter decomposition in freshwater habitats. For instance, growth of microbial populations on leaves that decompose rapidly can be compared to population dynamics on more recalcitrant leaves.

Soils are incubated with $^{18}O$-water for varying lengths of time, depending on the growth characteristics of the microbial community. Labeled DNA may not be detected if a soil sample is incubated too briefly. Using conventional methods of SIP detection, Blazewicz et al. found that labeled DNA could be detected 24 hours after $^{18}O$-water was added but not 3 hours after wet up (Blazewicz S J, Schwartz E, Firestone M K: Growth and death of bacteria and fungi underlie rainfall-induced carbon dioxide pulses from seasonally dried soil. Ecology 2014, 95:1162-1172.). The longer a sample is incubated with $^{18}O$-water, the greater the potential for label turnover, as labeled oxygen atoms incorporated into biomolecules of growing micro-organisms are consumed by other growing populations, creating a scenario where some organisms are incorporating $^{18}O$ from both water and organic substrates. This recycling of $^{18}O$ atoms may explain why, after longer incubations, three DNA bands can appear following ultracentrifugation. In contrast to SIP studies in temperate soils, longer incubations may be needed to detect growth in polar ecosystems. In the McMurdo Dry Valleys, soils were incubated with $^{18}O$-water in the field for 30 days because bacterial growth rates at freezing temperatures were very low.

Figure 15:
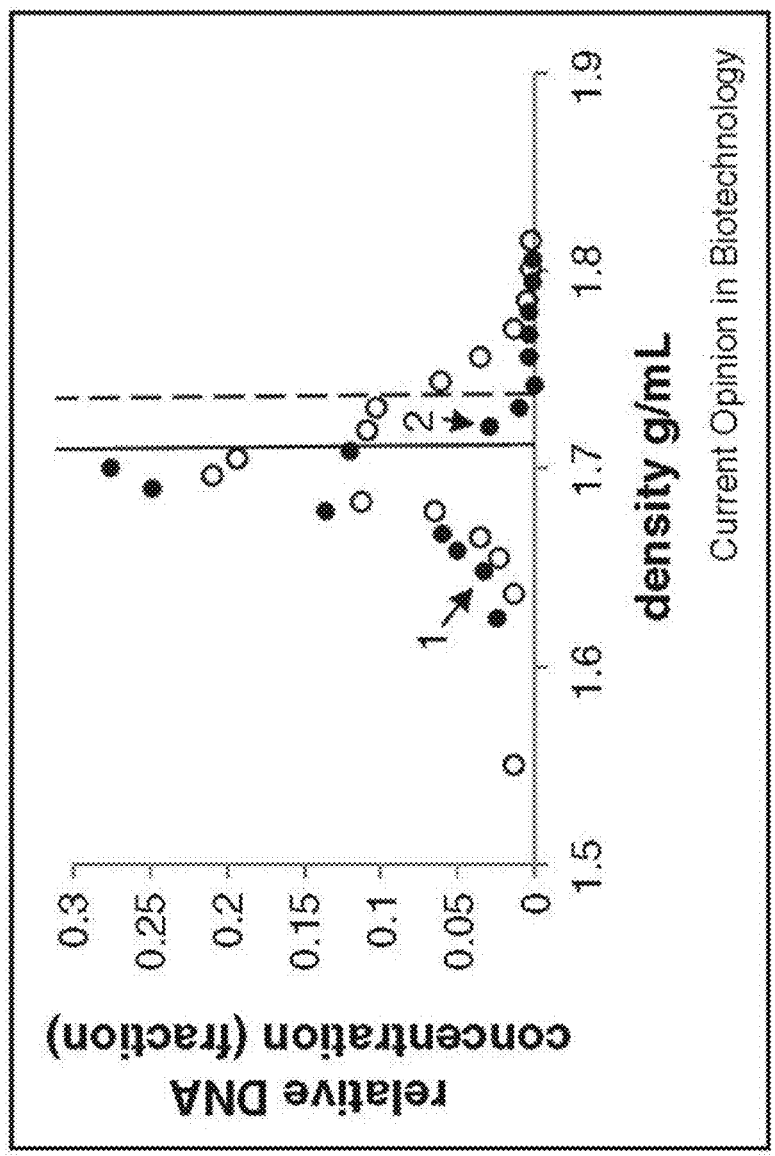
FIG. 15: Community density profiles of a control sample (*) to which non-labeled water was added and a treatment sample (*) to which $^{18}O$-water was added. The solid and dashed lines represent density thresholds that could separate the labeled heavy fractions from the non-labeled light fractions. The control samples marked with '1' or '2' are used in the text to explain how these subjective thresholds will bias the results against organisms with low GC genomes or in favor of organisms with high GC genomes. DNA was quantified through fluorimetry.

After incubation, nucleic acids are extracted from soil and separated along a cesium chloride gradient through isopycnic centrifugation. DNA will distribute along the gradient according to the guanine-cytosine (GC) content of the DNA, which affects its buoyant density in cesium chloride (Schildkraut C L: Determination of base composition of deoxyribonucleic acid from its buoyant density in CsCl. J Mol Biol 1962, 4:430, Buckley D H, Huangyutitham V, Hsu S-F, Nelson T A: Stable isotope probing with 15N achieved by disentangling the effects of genome G+C content and isotope enrichment on DNA Density. Appl Environ Microbiol 2007, 73:3189-3195.). The DNA will also distribute along the gradient according to the extent of labeling with $^{18}O$ atoms. After centrifugation, each sample is divided into density fractions, and the density and DNA concentration of each fraction are determined (Luders T. Manefield M, Friedrich M W: Enhanced sensitivity of DNA- and rRNA-based stable isotope probing by fractionation and quantitative analysis of isopycnic centrifugation gradients. Environ Microbiol 2004, 6:73-78.). Earlier SIP studies used fluorescent stains to visualize DNA bands, but gradient fractionation is now preferred because it provides a more precise comparison of labeled and non-labeled samples. The DNA concentration is graphed versus the density in each fraction to generate a community density graph (FIG. 15). The DNA in fractions from soil incubated with $^{18}O$-water generally have higher densities than DNA in fractions from soil incubated with natural abundance water. This shift in density indicates that the nucleic acids have become labeled with the heavy isotope. Sequencing the fractions where the shift is most apparent then reveals the taxa that are more abundant in the denser fractions of the labeled treatments compared to the unlabeled treatments; these taxa have assimilated the label and, in the case of SIP with $^{18}O$-water, have grown during the incubation.

Quantifying Microbial Growth with $^{18}O$-Water SIP

In any SIP experiment, the mere presence of a taxon's 16S rRNA gene in a high-density fraction does not confirm that the population has incorporated the heavier isotope during the incubation. It is critical to show that the taxon's genome has a higher concentration of the heavier isotope in the labeled treatment than in the control. In other words, it is essential to isolate the incorporation of the isotope tracer into a microbial population from natural variation in genomic GC content. In the community density graph shown in FIG. 15, a researcher may elect to use the density threshold indicated by the solid line. At densities above this threshold, DNA concentrations in the labeled treatment clearly are much higher than those in the control treatment. Alternatively, it would also be reasonable to select the density threshold described by the dashed line in FIG. 15 after which DNA concentrations in the control samples approach the detection limit. Regardless of which threshold is used, subsequent analyses will likely include errors where either a taxon will be identified as growing when it has not, or identified as not growing when in fact it has. Taxa with genomes of low GC content, like those abundant in the fraction labeled with a '1' in FIG. 15, will occur in less dense fractions in the cesium chloride gradient (i.e. toward the left of the density graph). These taxa will need to strongly assimilate the heavy isotope to become sufficiently labeled to cross the threshold into the heavy fraction. Consequently, it is likely these taxa will be characterized as non-growing even when they have produced new DNA and assimilated substantial quantities of the heavier isotope. In contrast, taxa with genomes of higher GC content, such as taxa abundant in the fraction labeled with a '2' in FIG. 15, will have to assimilate far less heavy isotope to be identified as growing. Thus, there is potential bias in this classic SIP approach toward identifying high-GC organisms as labeled and low-GC organisms as non-labeled. This bias applies to any SIP experiment interpreted this way, whether it uses $^{18}O$, $^{13}C$. or other tracers. Past studies account for this potential bias by using analyses of all fractions through DNA fingerprinting or pyrosequencing to identify specific microbial populations that become labeled. These studies quantified label incorporation by measuring density shifts of a taxon's genome during SIP experiments.

Figure 16:
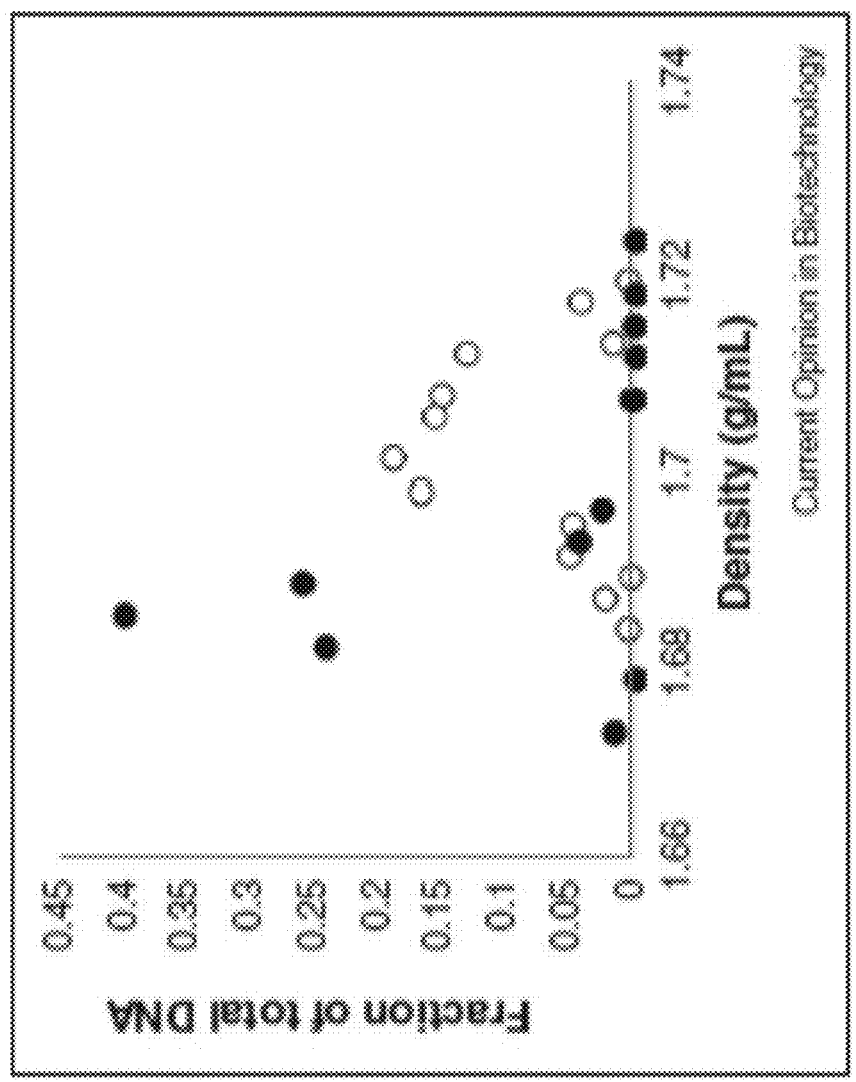
FIG. 16: A taxon density curve for the genus *Arthrobacter* is calculated by multiplying the proportion of the taxon's sequences in a sequencing library with the total number of 16S rRNA genes in a SIP fraction as measured with quantitative PCR. Fractions from a sample incubated with non-labeled water are represented by filled symbols while fractions from a sample incubated with $^{18}$O-water are labeled with open symbols.

By dividing density fractions qualitatively into only labeled or non-labeled DNA, all quantitative information about heavy isotope assimilation is lost. Soil microbial taxa presumably grow at different rates and therefore assimilate different quantities of $^{18}O$ during SIP experiments. An alternative to identifying each taxon as either growing or non-growing is to transform the typical, categorical response, to a continuous one that directly relates to growth. Quantitative SIP (qSIP) is an experimental approach that avoids the pitfalls of assigning heavy and light fractions and retains the quantitative information of the extent to which each taxon is labeled with $^{18}O$. From this quantitative assessment of labeling, it is feasible to estimate a growth rate for each taxon. Instead of splitting the density gradient into heavy and light fractions, in qSIP each fraction is sequenced separately for a target gene, like the 16S rRNA gene. Taxon density curves (FIG. 16) are then produced by multiplying the proportion of a taxon's 16S rRNA sequence by the total number of 16S rRNA gene copies as determined through qPCR. As in standard SIP, samples without a heavy isotope are compared to those with an added heavy isotope. The shift between these curves provides a basis for quantifying the change in density for each individual taxon caused by isotope incorporation. Because the density shift is calculated relative to the taxon's density measured without the added isotope tracer, this approach quantifies the degree of labeling for all taxa, regardless of GC content. This sets the stage for exploring taxonomic variation in a fundamental ecological trait: growth rate.

Using $^{18}O$-Water SIP to Study Microbial Death and Turnover

There are two different strategies to study microbial mortality through SIP with $^{18}O$-water. First, one can estimate the abundance of a taxon in non-labeled DNA at the beginning and end of an incubation. Populations that have declined in abundance during the incubation include individuals that have died, and their DNA will have been degraded. This approach measures mortality in non-growing microbial populations. It is important to confirm that the decline in abundance is real, and that the genome of the taxon has not simply increased in density because it was labeled and shifted to another part of the density profile, causing an apparent decline in the lower density region. This is another advantage of the qSIP approach, because the abundance of a given taxon across all density regions is assessed. This approach also assumes that all non-labeled DNA is part of viable non-growing cells, while it is likely that a fraction of non-labeled DNA is extracellular or present in non-viable but intact cells. A second approach is to first label DNA of growing cells with $^{18}O$ by incubating a soil sample in $^{18}O$-water, after which the labeled water can be repeatedly flushed out of the soil with unlabeled water. Subsequently, the decline in $^{18}O$ content of the DNA, which represents mortality of newly grown cells, can be measured through isotope ratio mass spectrometry (IRMS) analysis, or through qSIP on a taxon-specific basis. This approach would miss mortality of intact cells that have died but with DNA that has not yet been degraded. Interestingly, the few SIP studies that have considered mortality show large turnover rates of the microbial community, with as much as half of microorganisms dying within a week.

RNA-SIP with $^{18}O$-water to characterize RNA dynamics in microbial populations Studies of RNA-SIP with $^{18}O$-water have been conducted recently. Angel and Conrad studied the activation cascade in soil crusts by characterizing organisms that produced new ribosomal RNA after soil crusts were rewetted with $^{18}O$-water. SIP analysis of an incubation time series showed that not all populations produce new rRNA instantaneously, indicating that there is an ordered progression of reactivation of microbial populations as soil crusts are rewetted. Rettedal and Brozel (Rettedal E A, Bro"zel V S: Characterizing the diversity of active bacteria in soil by comprehensive stable isotope probing of DNA and RNA with H218O. Microbiology 2015, 4:208-219.) compared growing bacterial populations to bacterial populations that made new ribosomes as revealed by DNA SIP or rRNA SIP with $^{18}O$-water. They incubated soil samples for 38 days and found that both DNA and rRNA SIP identified similar communities, indicating that most dominant OTUs in the total nucleic acid extracts contained active members. Thirty-eight days is a long time to expose a microbial community to a labeled tracer, and it is likely that the label was recycled as microbial biomass turned over during the incubation. RNA SIP can offer a different perspective of microbial activity than DNA SIP because it only requires organisms to utilize the substrate in assimilatory processes, and because RNA labeling occurs more rapidly, allowing for shorter incubation periods. The use of non-labeled rRNA analysis as an activity measure has been challenged by other researchers. It is likely that RNA SIP with $^{18}O$-water will change our perspectives of RNA dynamics and microbial activity in soil.

We claim:

1. A method to quantify uptake of a substrate by a taxon in a microorganism sample, comprising:
   (a) extracting nucleic acids from a first microorganism sample that has been incubated with at least one isotopically labeled substrate and from a second microorganism sample that has not been incubated with an isotopically labeled substrate, thereby obtaining a labeled sample and an unlabeled sample;
   (b) separating said nucleic acids extracted from said first microorganism sample by density into a plurality of labeled fractions;
   (c) separating said nucleic acids extracted from said second microorganism sample by density into a plurality of unlabeled fractions;
   measuring a density of said nucleic acids from each of the fractions obtained in steps (b) and (c);
   (d) detecting a target sequence of a taxon of a microorganism in the fractions obtained in steps (b) and (c), whereby the presence of the taxon of a microorganism is determined;
   (e) measuring the relative abundance of the taxon of the microorganism in each of the fractions obtained in steps (b) and (c) through sequencing the target sequence;
   (f) quantifying through quantitative PCR an average density of said taxon of said microorganism in said fractions obtained in steps (b) and (c); and
   (g) measuring the difference between the average density of said taxon of said microorganism in the plurality of labeled fractions and the average density of said taxon of said microorganism in the corresponding plurality of unlabeled fractions; wherein said difference in average density is indicative of the quantity of said substrate taken up by said taxon of said microorganism.

2. The method of claim 1, wherein said first microorganism sample and said second microorganism sample are derived from soil incubation.

3. The method of claim 1, wherein said first microorganism sample and said second microorganism sample are derived from leaf decomposition.

4. The method of claim 1, wherein said first microorganism sample and said second microorganism sample comprise bacteria.

5. The method of claim 1, wherein separating nucleic acids by density is performed by centrifugation.

6. The method of claim 1, wherein the isotopically labeled substrate is selected from the group consisting of one or more of $^{18}$O-enriched water ($H_2O$), $^{13}$C-enriched glucose ($C_6H_{12}O_6$), and $^{15}$N-enriched ammonium chloride ($NH_4Cl$).

7. The method of claim 6, wherein the isotopically labeled substrate is about 97 atom % $^{18}$O-enriched $H_2O$.

8. The method of claim 1, wherein said density changes between the density of said taxon of said microorganism in unlabeled fractions and the density of said taxon of said microorganism in the corresponding labeled fractions are separated from density changes resulting from different GC (guanine-plus-cytosine) content.

9. The method of claim 1, wherein said separating nucleic acids by density into a plurality of fractions comprises obtaining about 5 to 75 fractions.

10. The method of claim 1, wherein the target sequence is a 16S rRNA gene sequence.

* * * * *